US009488625B2

(12) United States Patent
Felgenhauer et al.

(10) Patent No.: US 9,488,625 B2
(45) Date of Patent: Nov. 8, 2016

(54) PURIFICATION OF FACTOR VIII USING A CONDUCTIVITY GRADIENT

(75) Inventors: Martin Felgenhauer, Vienna (AT); Helmut Maierhofer, Gols (AT); Dominique Mison, Fontaines (CH); Arnaud Desponds, Yverdon-les-bains (CH)

(73) Assignees: Baxalta GmbH, Opfikon (CH); Baxalta Incorporated, Bannockburn, IL (US)

( * ) Notice: Subject to any disclaimer, the term of this patent is extended or adjusted under 35 U.S.C. 154(b) by 158 days.

(21) Appl. No.: 13/325,778

(22) Filed: Dec. 14, 2011

(65) Prior Publication Data
US 2012/0184715 A1 Jul. 19, 2012

Related U.S. Application Data

(60) Provisional application No. 61/423,509, filed on Dec. 15, 2010.

(51) Int. Cl.
| | |
|---|---|
| *G01N 30/96* | (2006.01) |
| *B01D 15/16* | (2006.01) |
| *B01D 15/36* | (2006.01) |
| *C07K 1/18* | (2006.01) |
| *C07K 14/755* | (2006.01) |
| *G01N 30/34* | (2006.01) |
| *G01N 30/80* | (2006.01) |
| *G01N 30/88* | (2006.01) |

(52) U.S. Cl.
CPC ............ *G01N 30/96* (2013.01); *B01D 15/166* (2013.01); *B01D 15/362* (2013.01); *B01D 15/363* (2013.01); *C07K 1/18* (2013.01); *C07K 14/755* (2013.01); *G01N 30/34* (2013.01); *G01N 30/80* (2013.01); *G01N 2030/8831* (2013.01)

(58) Field of Classification Search
None
See application file for complete search history.

(56) References Cited

U.S. PATENT DOCUMENTS

| | | | |
|---|---|---|---|
| 4,578,218 A * | 3/1986 | Saundry et al. ............ 530/383 |
| 5,061,789 A | 10/1991 | Moller et al. | |
| 5,071,961 A | 12/1991 | Kraus et al. | |
| 5,096,593 A | 3/1992 | Wakita et al. | |
| 5,110,907 A | 5/1992 | Kosow et al. | |
| 5,179,199 A | 1/1993 | Zabrecky et al. | |
| 5,214,033 A | 5/1993 | Zimmerman et al. | |
| 5,252,709 A | 10/1993 | Burnouf et al. | |
| 5,281,661 A | 1/1994 | Linnau et al. | |
| 5,288,853 A | 2/1994 | Bhattacharva et al. | |
| 5,300,433 A | 4/1994 | Hrinda et al. | |
| 5,304,638 A | 4/1994 | Marshall et al. | |
| 5,317,092 A | 5/1994 | Markussen | |
| 5,344,918 A | 9/1994 | Dazey et al. | |
| 5,378,365 A | 1/1995 | Arrighi et al. | |
| 5,408,039 A | 4/1995 | Burnouf-Radosevich et al. | |
| 5,445,958 A | 8/1995 | Feldman | |
| 5,457,181 A | 10/1995 | Michalski et al. | |
| 5,468,847 A | 11/1995 | Heilmann et al. | |
| 5,470,954 A | 11/1995 | Neslund et al. | |
| 5,506,341 A | 4/1996 | Newman et al. | |
| 5,597,711 A | 1/1997 | Zimmerman et al. | |
| 5,639,857 A | 6/1997 | Zimmermann | |
| 5,659,017 A | 8/1997 | Bhattacharya et al. | |
| 5,683,916 A | 11/1997 | Goffe et al. | |
| 5,714,583 A | 2/1998 | Foster et al. | |
| 5,733,873 A | 3/1998 | Osterberg et al. | |
| 5,760,183 A | 6/1998 | Dazey et al. | |
| 5,760,189 A | 6/1998 | Vicik et al. | |
| 5,847,086 A | 12/1998 | Farb et al. | |
| 5,851,400 A | 12/1998 | Frey et al. | |
| 5,880,265 A | 3/1999 | Fischer et al. | |
| 5,892,005 A | 4/1999 | Fischer et al. | |
| 5,906,747 A | 5/1999 | Coffman et al. | |
| 5,990,284 A | 11/1999 | Mahiou et al. | |
| 5,990,289 A | 11/1999 | Fauquex et al. | |
| 6,005,082 A | 12/1999 | Smeds | |
| 6,034,222 A | 3/2000 | Fischer et al. | |
| 6,063,909 A | 5/2000 | Huang et al. | |
| 6,096,872 A | 8/2000 | Van Holten et al. | |
| 6,143,179 A | 11/2000 | Muller-Berghaus et al. | |
| 6,265,542 B1 | 7/2001 | Fahrner et al. | |
| 6,307,032 B1 | 10/2001 | Schonhofer et al. | |
| 6,358,534 B1 | 3/2002 | Schwarz et al. | |
| 6,414,125 B1 | 7/2002 | Siekmann et al. | |
| 6,428,703 B1 | 8/2002 | Zinn et al. | |
| 6,444,788 B1 | 9/2002 | Staby | |
| 6,465,624 B1 | 10/2002 | Fischer et al. | |
| 6,492,105 B2 | 12/2002 | Yu et al. | |
| 6,579,723 B1 | 6/2003 | Mitterer et al. | |
| 6,670,455 B1 | 12/2003 | Roemisch et al. | |
| 6,677,440 B1 | 1/2004 | Roemisch et al. | |
| 6,683,159 B2 | 1/2004 | Kelley et al. | |

(Continued)

FOREIGN PATENT DOCUMENTS

| | | |
|---|---|---|
| CA | 2 570 956 A1 | 6/2008 |
| EP | 0 346 241 A1 | 12/1989 |

(Continued)

OTHER PUBLICATIONS

AKTAFPLC System Manual. 2000. Amersham Pharmacia Biotech. 1-61.*

(Continued)

*Primary Examiner* — Paul Holland

(74) *Attorney, Agent, or Firm* — K&L Gates LLP; Louis C. Cullman; Georgia N. Kefallinos

(57) ABSTRACT

The present specification discloses methods of eluting a protein from a chromatography column.

5 Claims, No Drawings

(56) References Cited

U.S. PATENT DOCUMENTS

| | | |
|---|---|---|
| 6,777,390 B1 | 8/2004 | Matthiessen et al. |
| 6,844,201 B2 | 1/2005 | Malmqvist et al. |
| 6,893,856 B2 | 5/2005 | Josic et al. |
| 6,924,151 B2 | 8/2005 | Fischer et al. |
| 6,946,075 B2 | 9/2005 | Kopf |
| 7,026,453 B2 | 4/2006 | Haj-Ahmad |
| 7,166,709 B2 | 1/2007 | Josic et al. |
| 7,276,590 B1 | 10/2007 | Staby |
| 7,347,943 B2 | 3/2008 | Herman |
| 7,374,684 B2 | 5/2008 | Gibson et al. |
| 7,422,865 B2 | 9/2008 | Fischer |
| 7,427,659 B2 | 9/2008 | Shukla et al. |
| 7,439,337 B2 | 10/2008 | Ward |
| 7,531,513 B2 | 5/2009 | Grancha Gamon et al. |
| 7,648,958 B2 | 1/2010 | Mitterer et al. |
| 2002/0025556 A1* | 2/2002 | Fischer et al. ............... 435/69.1 |
| 2002/0035241 A1 | 3/2002 | Buchacher et al. |
| 2003/0091976 A1 | 5/2003 | Boschetti et al. |
| 2004/0241721 A1 | 12/2004 | Gjerde et al. |
| 2005/0064513 A1 | 3/2005 | Haynes et al. |
| 2005/0165221 A1 | 7/2005 | Booth et al. |
| 2005/0269297 A1 | 12/2005 | Voute et al. |
| 2006/0036081 A1 | 2/2006 | Martel et al. |
| 2006/0094098 A1 | 5/2006 | Yamaoka et al. |
| 2006/0229437 A1 | 10/2006 | Senczuk et al. |
| 2006/0246544 A1 | 11/2006 | Kang et al. |
| 2007/0037966 A1 | 2/2007 | Rasmussen et al. |
| 2007/0039891 A1 | 2/2007 | Boschetti et al. |
| 2007/0299250 A1 | 12/2007 | Kretschmar et al. |
| 2007/0299251 A1 | 12/2007 | Lihme |
| 2008/0066530 A1 | 3/2008 | Eckermann et al. |
| 2008/0090995 A1 | 4/2008 | Andersson et al. |
| 2008/0151544 A1 | 6/2008 | Tabuchi et al. |
| 2008/0167452 A1 | 7/2008 | Maiti et al. |
| 2008/0176312 A1 | 7/2008 | Laemmle et al. |
| 2008/0206225 A1 | 8/2008 | Arentsen et al. |
| 2008/0207879 A1 | 8/2008 | Mitterer et al. |
| 2008/0210614 A1 | 9/2008 | Gilar et al. |
| 2008/0220532 A1 | 9/2008 | Alpert |
| 2008/0253992 A1 | 10/2008 | DeFrees et al. |
| 2008/0269469 A1 | 10/2008 | Yanagisawa et al. |
| 2009/0029918 A1 | 1/2009 | Mundt et al. |
| 2009/0036652 A1 | 2/2009 | Rasmussen et al. |
| 2009/0043080 A1 | 2/2009 | Clausen et al. |
| 2009/0047723 A1 | 2/2009 | Jensen et al. |
| 2009/0126466 A1 | 5/2009 | Gilar et al. |
| 2009/0145203 A1 | 6/2009 | Vorm et al. |
| 2009/0149638 A1 | 6/2009 | Ley et al. |
| 2009/0232737 A1 | 9/2009 | Moya et al. |
| 2009/0242750 A1 | 10/2009 | Axelman et al. |
| 2009/0311239 A1 | 12/2009 | Chtourou et al. |
| 2010/0024527 A1 | 2/2010 | LaMarr et al. |
| 2010/0042038 A1 | 2/2010 | Urdahl et al. |
| 2010/0056744 A1 | 3/2010 | Monrabal Bas |
| 2010/0075375 A1 | 3/2010 | Defrees et al. |

FOREIGN PATENT DOCUMENTS

| | | |
|---|---|---|
| EP | 0 600 480 A2 | 6/1994 |
| EP | 0 934 748 A2 | 8/1999 |
| EP | 1 900 751 A1 | 3/2008 |
| EP | 2 027 875 A1 | 2/2009 |
| JP | 03155797 A2 | 3/1991 |
| JP | H07-215998 A | 8/1995 |
| JP | 10059867 A2 | 3/1998 |
| KR | 2009113825 A | 2/2009 |
| KR | 2010028042 A | 3/2010 |
| RU | 2 163 140 C1 | 2/2001 |
| WO | 91/07438 A1 | 5/1991 |
| WO | 93/03147 A1 | 2/1993 |
| WO | 93/15105 A1 | 8/1993 |
| WO | 94/01120 A1 | 1/1994 |
| WO | 95/12609 A1 | 5/1995 |
| WO | 96/25490 A1 | 8/1996 |
| WO | 98/01464 A1 | 1/1998 |
| WO | 98/23645 A1 | 6/1998 |
| WO | 98/38218 A1 | 9/1998 |
| WO | 99/21889 A1 | 5/1999 |
| WO | 99/31138 A1 | 6/1999 |
| WO | 99/42193 A1 | 8/1999 |
| WO | 99/51724 A1 | 10/1999 |
| WO | 00/27496 A1 | 5/2000 |
| WO | 2006/023831 A2 | 3/2006 |
| WO | 2006/067230 A1 | 6/2006 |
| WO | 2008/073620 A2 | 6/2008 |
| WO | 2008/087184 A2 | 7/2008 |
| WO | 2008/102923 A1 | 8/2008 |
| WO | 2008/106043 A2 | 9/2008 |
| WO | 2008/143977 A1 | 11/2008 |
| WO | 2009/007451 A1 | 1/2009 |
| WO | 2009/014481 A1 | 1/2009 |
| WO | 2009/016431 A1 | 2/2009 |
| WO | 2009/024620 A2 | 2/2009 |
| WO | 2009/030866 A2 | 3/2009 |
| WO | 2009/032293 A1 | 3/2009 |
| WO | 2009/058769 A1 | 5/2009 |
| WO | 2009/063069 A2 | 5/2009 |
| WO | 2009/091680 A1 | 7/2009 |
| WO | 2009/138488 A1 | 11/2009 |
| WO | 2009/141384 A2 | 11/2009 |
| WO | 2009/156730 A1 | 12/2009 |
| WO | 2010/014970 A1 | 2/2010 |

OTHER PUBLICATIONS

Olthuis W et al. Differential measuring using an ion exchanger applied to Ca2+ ion concentration determination. 2003. Sensors and Actuators B. 89:53-57.*

International Search Report. PCT/US2011/064962. May 8, 2012.

Singapore Search Report for Singapore Patent Application No. 201304628-9 filed on Dec. 14, 2011.

\* cited by examiner

PURIFICATION OF FACTOR VIII USING A CONDUCTIVITY GRADIENT

PRIORITY CLAIM

This patent application claims priority pursuant to 35 U.S.C. §119(e) to U.S. Provisional Patent Application Ser. No. 61/423,509 filed Dec. 15, 2010, which is hereby incorporated by reference in its entirety.

FIELD

The present specification relates to methods of purifying a protein during a manufacturing process.

INTRODUCTION

Ion-exchange chromatography (or ion chromatography) is a process that allows the separation of ions and polar molecules based on their charge. This type of chromatography is further subdivided into cation exchange chromatography and anion exchange chromatography. It can be used for almost any kind of charged molecule including large polypeptides, small nucleotides and amino acids. The solution to be injected is usually called a sample, and the individually separated components are called analytes. It is often used in protein purification, water analysis, and quality control. Ion exchange chromatography retains analytes on the column based on coulombic (ionic) interactions.

Generally, a sample comprising an ionic compound including a cationic species $M^+$ and an anionic species $B^-$ is introduced, either manually or with an autosampler, into a sample loop of known volume. A buffered aqueous solution known as the mobile phase carries the sample from the loop onto a column that contains some form of stationary phase material. This is typically a resin or gel matrix comprising agarose or cellulose beads with covalently bonded charged functional groups (R—X). The ionic functional groups of the beads interact with analyte ions of opposite charge in such a manner that the analyte is retained by the stationary phase. In cation exchange chromatography, the column retains positively charged cations because the stationary phase displays a negatively charged functional group, e.g., $R-X^-C^+ + M^+B^- \leftrightarrow R-X^-M^+ + C^+ + B^-$. In anion exchange chromatography, the column retains negatively charged anions because the stationary phase displays a positively charged functional group, e.g., $R-X^+A^- + M^+B^- \leftrightarrow R-X^+B^- + M^+ + A^-$. The retained target analytes (anions or cations) can be subsequently eluted from the column by increasing the ion concentration of a similarly charged species that will displace the analyte ions from the stationary phase. For example, in cation exchange chromatography, the positively charged analyte could be displaced by the addition of positively charged sodium ions. Similarly, in anion exchange chromatography, the negatively charged analyte could be displaced by the addition of negatively charged chloride ions. The elution must then be assayed for the analytes of interest by some form of detected method, typically by electrical conductivity or UV/Visible light absorbance.

Because polypeptides have numerous functional groups that can have both positive and negative charges, ion exchange chromatography separates proteins according to their net charge. The net charge of a polypeptide is dependent on the composition of the mobile phase. By adjusting the pH of the mobile phase, the net charge of a polypeptide of interest will become one that enables its interaction with the charged stationary phase of the column. For example, if a polypeptide has a net positive charge over pH 7, then it will bind to a column of a negatively-charged stationary phase, whereas a negatively charged polypeptide would not. Elution of a polypeptide also occurs by altering its net charge, which is also achieved by changing the pH or the ionic concentration of the mobile phase. For example, to elute a polypeptide bound to negatively-charged stationary phase, the pH of the mobile phase is altered in a manner that causes the net charge on the polypeptide to become negative. Elution by changing the ionic strength of the mobile phase occurs as ions from the mobile phase preferentially interact with ions on the polypeptide over ions from the negatively-charged stationary phase. This interaction "shields" the polypeptide from the stationary phase ions, thereby allowing the polypeptide to elute.

Elution of a polypeptide by changing the pH or ion concentration of the mobile phase has several drawbacks. First, protein elution by pH or ion concentration alteration is a time consuming process. For example, detection of a protein of interest by electrical conductivity or UV/Visible light absorbance must occur during the entire elution process because release of the polypeptide of interest from the stationary phase by pH or ion concentration alteration is variable. As such, eluate collection must occurs over a consecutive series of multiple fractions, typically up to 24 fractions, and each fraction is then analyzed to identify fractions containing a threshold amount of the polypeptide of interest, and this subset is then pooled for subsequent processing. This elution process itself is time consuming. Additionally, a long period of hold time occurs between the eluate collection and pooling steps. Second, the long period of time necessary to elute a polypeptide of interest by changing the pH or ion concentration increases a protein's susceptibility to protein degradation, thereby resulting in decreased protein yields. Third, protein elution by pH or ion concentration alteration is a labor intensive process requiring an open system where an operator can access the fraction collector to avoid mechanical incident. Forth, there is a risk of human error during the calculation of the fractions to be pooled or during the manual pooling itself.

The present specification discloses a novel elution collection method that addresses these drawbacks. The method disclosed herein uses a conductivity gradient to initiate and stop the elution collection process. This conductivity gradient "trigger" automatically recovers a protein of interest from a column as a single fraction eluate. The elution collection method disclosed herein decreasing the elution time necessary to collect a protein of interest from an ion exchange column, eliminates the hold time that occurs between the eluate collection and pooling steps, and allows for a closed system design. As such, the disclosed elution collection improves protein yields by reducing its susceptibility to degradation or its loss due to mechanical incident or human error.

SUMMARY

Thus, aspects of the present specification disclose a method of collecting an elution from a column, the method comprising the steps of: a) applying a sample comprising a protein to a cation exchange chromatography column, wherein the application causes the protein to be retained by the column; b) applying a mobile phase to the cation exchange chromatography column, the mobile phase comprising a buffered solution, wherein application of the mobile phase establishes a conductivity gradient of from about 8 mS/cm to about 90 mS/cm; c) starting an eluate collection when an inlet conductivity value measured for the mobile phase entering the cation exchange chromatography column is from about 25.0 mS/cm to about 27.0 mS/cm; and d) stopping the eluate collection when the inlet conductivity value measured for the mobile phase entering the cation exchange chromatography column is from about 41.0 mS/cm to about 43.0 mS/cm; wherein the eluate collection comprises at least 25% of the protein retained by the cation exchange chromatography column in step (a). The buffered solution disclosed herein can further comprise an electrolyte and/or a surfactant. The electrolyte disclosed herein may comprise sodium ions, potassium ions, calcium ions, magnesium ions, chloride ions, hydrogen phosphate ions, hydrogen carbonate ions, or any combination thereof. The surfactant disclosed herein can be an ionic surfactant like an anion surfactant or cationic surfactant, a zwitterionic (amphoteric) surfactant, or a non-ionic surfactant. The conductivity gradient disclosed herein can be defined by a linear function, a sigmoidal function, a logarithmic function, or an exponential function. The method can be performed as a closed system.

Other aspects of the present specification disclose a method of collecting an elution from a column, the method comprising the steps of: a) applying a sample comprising a protein to a cation exchange chromatography column, wherein the application causes the protein to be retained by the column; b) applying a mobile phase to the cation exchange chromatography column, the mobile phase comprising a buffered solution, wherein application of the mobile phase establishes a conductivity gradient of from about 8 mS/cm to about 90 mS/cm; c) starting an eluate collection when an outlet conductivity value measured for the mobile phase exiting the cation exchange chromatography column is from about 19.0 mS/cm about 21.0 mS/cm; and d) stopping the eluate collection when the outlet conductivity value measured for the mobile phase exiting the cation exchange chromatography column is from about 34.5 mS/cm to about 36.5 mS/cm; wherein the eluate collection comprises at least 25% of the protein retained by the cation exchange chromatography column in step (a). The method can be performed as a closed system.

Yet other aspects of the present specification disclose a method of collecting an elution from a column, the method comprising the steps of: a) applying a sample comprising a protein to an anion exchange chromatography column, wherein the application causes the protein to be retained by the column; b) applying a mobile phase to the anion exchange chromatography column, the mobile phase comprising a buffered solution, wherein application of the mobile phase establishes a conductivity gradient of from about 4 mS/cm to about 80 mS/cm; c) starting an eluate collection when an inlet conductivity value measured for the mobile phase entering the anion exchange chromatography column is from about 27.8 mS/cm to about 29.8 mS/cm; and d) stopping the eluate collection when the inlet conductivity value measured for the mobile phase entering the anion exchange chromatography column is from about 51.0 mS/cm to about 53.0 mS/cm; wherein the eluate collection comprises at least 25% of the protein retained by the anion exchange chromatography column in step (a). The method can be performed as a closed system.

Yet other aspects of the present specification disclose a method of collecting an elution from a column, the method comprising the steps of: a) applying a sample comprising a protein to an anion exchange chromatography column, wherein the application causes the protein to be retained by the column; b) applying a mobile phase to the anion exchange chromatography column, the mobile phase comprising a buffered solution, wherein application of the mobile phase establishes a conductivity gradient of from about 4 mS/cm to about 80 mS/cm; c) starting an eluate collection when an outlet conductivity value measured for the mobile phase exiting the column is from about 21.0 mS/cm to about 23.0 mS/cm; and d) stopping the eluate collection when the outlet conductivity value measured for the mobile phase exiting the column is from about 45.5 mS/cm to about 47.5 mS/cm; wherein single eluate collection comprises at least 25% of the protein retained by the anion exchange chromatography column in step (a). The method can be performed as a closed system.

Still other aspects of the present specification disclose a method of collecting an elution from a column, the method comprising the steps of: a) applying a sample comprising a protein to a cation exchange chromatography column, wherein the application causes the protein to be retained by the column; b) applying a mobile phase to the cation exchange chromatography column, the mobile phase comprising a buffered solution, wherein application of the mobile phase establishes a conductivity gradient of from about 8 mS/cm to about 90 mS/cm; c) starting an eluate collection when an inlet conductivity value measured for the mobile phase entering the cation exchange chromatography column is from about 25.0 mS/cm to about 27.0 mS/cm or an outlet conductivity value measured for the mobile phase exiting the cation exchange chromatography column is from about 19.0 mS/cm about 21.0 mS/cm; and d) stopping the eluate collection when the inlet conductivity value measured for the mobile phase entering the cation exchange chromatography column is from about 41.0 mS/cm to about 43.0 mS/cm or the outlet conductivity value measured for the mobile phase exiting the cation exchange chromatography column is from about 34.5 mS/cm to about 36.5 mS/cm; wherein the eluate collection comprises at least 25% of the protein retained by the cation exchange chromatography column in step (a). The method can be performed as a closed system.

Still other aspects of the present specification disclose a method of collecting an elution from a column, the method comprising the steps of: a) applying a sample comprising a protein to an anion exchange chromatography column, wherein the application causes the protein to be retained by the column; b) applying a mobile phase to the anion exchange chromatography column, the mobile phase comprising a buffered solution, wherein application of the mobile phase establishes a conductivity gradient of from about 4 mS/cm to about 80 mS/cm; c) starting an eluate collection when an inlet conductivity value measured for the mobile phase entering the anion exchange chromatography column is from about 27.8 mS/cm to about 29.8 mS/cm or an outlet conductivity value measured for the mobile phase exiting the anion exchange chromatography column is from about 21.0 mS/cm to about 23.0 mS/cm; and d) stopping the eluate collection when the inlet conductivity value measured for the mobile phase entering the anion exchange chromatography column is from about 51.0 mS/cm to about 53.0 mS/cm or the outlet conductivity value measured for the mobile phase exiting the anion exchange chromatography column is from about 45.5 mS/cm to about 47.5 mS/cm; wherein single eluate collection comprises at least 25% of the protein retained by the column in step (a). The method can be performed as a closed system.

Further aspects of the present specification disclose a method of collecting an elution from a column, the method comprising the steps of: a) applying a sample comprising a protein to a column, wherein the application causes the protein to be retained by the column; b) applying a mobile phase to the column, the mobile phase comprising a buffered solution, wherein application of the mobile phase establishes a conductivity gradient of from about 4 mS/cm to about 90 mS/cm; c) starting an eluate collection when an conductivity value measured for the mobile phase is from about 19.0 mS/cm to about 30.0 mS/cm; and d) stopping the eluate collection when the conductivity value measured for the mobile phase is from about 34.0 mS/cm to about 53.0 mS/cm; wherein the eluate collection comprises at least 25% of the protein retained by the column in step (a). The method can be performed as a closed system.

DESCRIPTION

Ion exchange chromatography is a chromatographical method that is widely used for chemical analysis and separation of charged molecules. Ion exchange is a reversible chemical reaction wherein an ion from a compound contained in a sample is exchanged for a similarly charged ion attached to an immobile ion-exchange resin of the stationary phase. An important area of the application is extraction and purification of biologically produced substances such as, e.g., amino acids, proteins, and polynucleotide molecule like DNA and RNA.

Ion exchange columns include a stationary phase, which typically comprises an ion-exchange resin fixed in place for the chromatography procedure, and a mobile phase, which comprises a buffered solution that moves in a definite direction during the chromatography procedure.

A stationary phase comprises an ion-exchange resin. Ion exchange resin is a an insoluble matrix (or support structure) normally in the form of small beads of about 1 mm to about 2 mm in diameter. The resin has highly developed structure of surface pores which serve as ion exchange sites that easily trapped and released ions. The trapping of ions takes place only with simultaneous releasing of other ions; thus the process is called ion-exchange. Ion exchange resins are classified as cation exchangers that have positively charged mobile ions available for exchange, and anion exchangers, that exchangeable ions are negatively charged. Both anion and cation resins are produced from the same organic polymers, such as, e.g., polystyrene. They differ in the ionizable group attached to the hydrocarbon network. It is this functional group that determines the chemical behavior of the resin. Resins can be broadly classified as strong or weak acid cation exchangers or strong or weak base anion exchangers. For example, strongly acidic cation resins typically comprise sulfonic acid groups, such as, e.g. sodium polystyrene sulfonate or polyAMPS; strongly basic anion resins include quaternary amino groups like trimethylammonium groups or trimethylbenzylammonium groups, such as, e.g. polyAPTAC; weakly acidic cation resins comprise carboxylic acid groups; and weakly basic anion resins include primary, secondary, and/or ternary amino groups, such as, e.g. polyethylene amine.

Most typical ion-exchange resins are based on crosslinked organic polymers, such as, e.g., polystyrene. The required functional groups can be introduced after polymerization, or substituted monomers can be used. For example, crosslinking is often achieved by adding about 0.5% to about 25% of divinylbenzene to styrene at the polymerization process. Crosslinking decreases ion-exchange capacity of the resin and prolongs the time needed to accomplish the ion exchange processes. However, non-crosslinked polymers are only rarely used because they are less stable. Particle size also influences the resin parameters; smaller particles have larger outer surface, but cause larger head loss in the column processes.

A mobile phase comprises a buffered solution. Any buffer may be used, with the proviso that the resulting buffered solution is useful to practice the methods disclosed herein. A buffered solution can be varied as appropriate by one skilled in the art and generally depends, in part, on the pH value desired for the mobile phase, the protein being eluted, and the conductivity values being employed. Therefore, aspects of this embodiment may optionally include, e.g., 2-(N-morpholino) ethanesulfonic acid (MES), N-(2-acetamido)iminodiacetic acid (ADA), dimethylarsinic acid (Cacodylate), piperazine-N,N'-bis(2-ethanesulfonic acid) (PIPES), N-(2-Acetamido)-2-aminoethanesulfonic acid (ACES), cholamine chloride, N,N'-bis(2-hydroxyethyl)-2-aminoethanesulfonic acid (BES), 3-(N-morpholino) propanesulfonic acid (MOPS), 2-{[tris(hydroxymethyl)methyl]amino} ethanesulfonic acid (TES), N-(2-hydroxyethyl) piperazine-N'-(2-ethanesulfonic acid) (HEPES), piperazine-N,N'-bis(2-hydroxypropanesulfonic acid) (POPSO), N-tris (hydroxymethyl) methylglycine (Tricine), tris(hydroxymethyl)methylamine (Tris), acetamidoglycine, N,N-bis(2-hydroxyethyl)glycine (Bicine), N-tris(hydroxymethyl) methyl-3-aminopropanesulfonic acid (TAPS), 3-[(1,1-dimethyl-2-hydroxyethyl)amino]-2-hydroxypropanesulfonic acid (AMPSO), 3-(cyclohexylamino)-2-hydroxy-1-propanesulfonic acid (CAPSO), and 3-(cyclohexylamino)-1-propanesulfonic acid (CAPS); acetate buffers, such as, e.g., magnesium acetate, potassium acetate, and Tris acetate; borate buffers; citrate buffers; phosphate buffers, such as, e.g., potassium phosphate buffers and sodium phosphate buffers; saline buffers, such as, e.g., phosphate-buffered saline (PBS), HEPES-buffered saline (HBS), and Tris-buffered saline (TBS), saline sodium citrate (SSC); universal buffers, such as, e.g., buffers comprising citric acid and potassium phosphate, Britton-Robinson buffer, Carmody buffer and the like, or any combination thereof. Non-limiting examples of how to make and use specific buffers are described in, e.g., MOLECULAR CLONING, A LABORATORY MANUAL (Joseph Sambrook & David W. Russell eds., Cold Spring Harbor Laboratory Press, 3$^{rd}$ ed. 2001) and CURRENT PROTOCOLS IN MOLECULAR BIOLOGY (Frederick M. Ausubel et al., eds. John Wiley & Sons, 2004).

It is understood that acids or bases can be used to adjust the pH of a buffered solution disclosed herein as needed. In an aspect of this embodiment, an effective pH level of a buffered solution disclosed herein is, e.g., at least about pH 5.0, at least about pH 5.5, at least about pH 6.0, at least about pH 6.5, at least about pH 7.0 or at about pH 7.5. In another aspect of this embodiment, an effective pH level of a buffered solution disclosed herein is, e.g., at most about pH 5.0, at most about pH 5.5, at most about pH 6.0, at most about pH 6.5, at most about pH 7.0 or at most about pH 7.5. In yet another aspect of this embodiment, an effective pH level of a buffered solution disclosed herein is, e.g., about pH 5.0 to about pH 8.0, an effective pH level is about pH 5.0 to about pH 7.0, an effective pH level is about pH 5.0 to about pH 6.0, is about pH 5.5 to about pH 8.0, an effective pH level is about pH 5.5 to about pH 7.0, an effective pH level is about pH 5.5 to about pH 5.0, is about pH 5.5 to about pH 7.5, an effective pH level is about pH 5.5 to about pH 6.5.

A buffered solution disclosed herein may be of any concentration, with the proviso that the concentration is useful to practice the methods disclosed herein. The buffer concentration used in a method disclosed herein can be varied as appropriate by one skilled in the art and generally depends, in part, on the buffering capacity of a particular buffer being used, the protein being eluted, and the conductivity values being employed. In aspects of this embodiment, the concentration of a buffered solution is, e.g., at least 0.1 mM, at least 0.2 mM, at least 0.3 mM, at least 0.4 mM, at least 0.5 mM, at least 0.6 mM, at least 0.7 mM, at least 0.8 mM, or at least 0.9 mM. In other aspects of this embodiment, the buffer concentration of a buffered solution is, e.g., at least 1.0 mM, at least 2.0 mM, at least 3.0 mM, at least 4.0 mM, at least 5.0 mM, at least 6.0 mM, at least 7.0 mM, at least 8.0 mM, or at least 9.0 mM. In yet other aspects of this embodiment, the concentration of a buffered solution is, e.g., at least 10 mM, at least 20 mM, at least 30 mM, at least 40 mM, at least 50 mM, at least 60 mM, at least 70 mM, at least 80 mM, or at least 90 mM. In still other aspects of this embodiment, the concentration of a buffered solution is, e.g., at least 100 mM, at least 200 mM, at least 300 mM, at least 400 mM, at least 500 mM, at least 600 mM, at least 700 mM, at least 800 mM, or at least 900 mM.

In other aspects of this embodiment, the concentration of a buffered solution is, e.g., at most 0.1 mM, at most 0.2 mM, at most 0.3 mM, at most 0.4 mM, at most 0.5 mM, at most 0.6 mM, at most 0.7 mM, at most 0.8 mM, or at most 0.9 mM. In yet other aspects of this embodiment, the concentration of a buffered solution is, e.g., at most 1.0 mM, at most 2.0 mM, at most 3.0 mM, at most 4.0 mM, at most 5.0 mM, at most 6.0 mM, at most 7.0 mM, at most 8.0 mM, or at most 9.0 mM. In still other aspects of this embodiment, the concentration of a buffered solution is, e.g., at most 10 mM, at most 20 mM, at most 30 mM, at most 40 mM, at most 50 mM, at most 60 mM, at most 70 mM, at most 80 mM, or at most 90 mM. In further aspects of this embodiment, the concentration of a buffered solution is, e.g., at most 100 mM, at most 200 mM, at most 300 mM, at most 400 mM, at most 500 mM, at most 600 mM, at most 700 mM, at most 800 mM, or at most 900 mM.

In other aspects of this embodiment, the concentration of a buffered solution is between, e.g., about 0.1 mM to about 900 mM, 0.1 mM to about 500 mM, 0.1 mM to about 100 mM, 0.1 mM to about 90 mM, 0.1 mM to about 50 mM, 1.0 mM to about 900 mM, 1.0 mM to about 500 mM, 1.0 mM to about 100 mM, 1.0 mM to about 90 mM, or 1.0 mM to about 50 mM.

Aspects of the present specification disclose, in part, a conductivity gradient. The conductivity (or specific conductance) of a buffered solution is a measure of its ability to conduct electricity. The SI unit of conductivity is Siemens per meter (S/m). Typically, the conductivity gradient is contiuous or linear in that there is a constant and progressive increase in conductivity. The constant and progressive increase in conductivity leads to the progressive elution of the protein bound to the column according to their apparent net charge. For cation exchange chromatography, proteins having a low positive apparent net charge will elute first, while proteins having a high positive apparent net charge will elute last. For anion exchange chromatography, proteins having a low negative apparent net charge will elute first, while proteins having a high negative apparent net charge will elute last.

Any conductivity gradient may be used with the proviso that that the established conductivity gradient is useful to practice the methods disclosed herein. Generally, a conductivity gradient with a steep slope will result in an elution profile having a narrow peak, and thus starting and stopping conductivity values that are closer together. Conversely, conductivity gradient with a shallow slope will result in an elution profile having a broad peak, and thus starting and stopping conductivity values that are further apart. Typically a conductivity gradient can be defined by a mathematical function such as, e.g., an algebraic function like a linear function, a sigmoidal function, a polynomial function, a nth root function, or a rational function; a transcendental function like an exponential function, a hyperbolic function, or a logarithmic function; a power function; or a periodic function. A conductivity gradient having multiple sub-conductivity gradients mat also be employed. For example, a linear conductivity gradient can be established with a range of about 5 mS/cm to about 40 mS/cm, and then transition into an exponential conductivity gradient from about 40 mS/cm to about 90 mS/cm. The transition may be immediate, or may involve a steady-state mobile phase (i.e, without a gradient) of, e.g., 40 mS/cm. A conductivity gradient may also be a step gradient where a column is washed with a mobile phase having a low conductivity, such as, e.g., about 1 mS/cm to about 15 mS/cm, the protein is then eluted using a mobile phase having a conductivity, such as, e.g., about 25 mS/cm to about 35 mS/cm, and lastly the column is regenerated by washing with a mobile phase having a high conductivity, such as, e.g., about 80 mS/cm to about 90 mS/cm.

A conductivity gradient can have any starting conductivity, with the proviso that the starting conductivity establishes a conductivity gradient useful to practice the methods disclosed herein. In aspects of this embodiment, a conductivity gradient has a starting conductivity of, e.g., about 1 mS/cm, about 2 mS/cm, about 3 mS/cm, about 4 mS/cm, about 5 mS/cm, about 6 mS/cm, about 7 mS/cm, about 8 mS/cm, about 9 mS/cm, or about 10 mS/cm. In other aspects of this embodiment, a conductivity gradient has a starting conductivity of, e.g., at least 1 mS/cm, at least 2 mS/cm, at least 3 mS/cm, at least 4 mS/cm, at least 5 mS/cm, at least 6 mS/cm, at least 7 mS/cm, at least 8 mS/cm, at least 9 mS/cm, or at least 10 mS/cm. In yet other aspects of this embodiment, a conductivity gradient has a starting conductivity of between, e.g., about 1 mS/cm to about 3 mS/cm, about 1 mS/cm to about 5 mS/cm, about 2 mS/cm to about 4 mS/cm, about 2 mS/cm to about 6 mS/cm, about 3 mS/cm to about 5 mS/cm, about 3 mS/cm to about 7 mS/cm, about 4 mS/cm to about 6 mS/cm, about 4 mS/cm to about 8 mS/cm, about 5 mS/cm to about 7 mS/cm, about 5 mS/cm to about 9 mS/cm, about 6 mS/cm to about 8 mS/cm, about 6 mS/cm to about 10 mS/cm, about 7 mS/cm to about 9 mS/cm, about 7 mS/cm to about 11 mS/cm, about 8 mS/cm to about 10 mS/cm, about 8 mS/cm to about 12 mS/cm, about 9 mS/cm to about 11 mS/cm, or about 9 mS/cm to about 13 mS/cm.

A conductivity gradient can have any ending conductivity, with the proviso that the ending conductivity establishes a conductivity gradient useful to practice the methods disclosed herein. In aspects of this embodiment, a conductivity gradient has an ending conductivity of, e.g., about 50 mS/cm, about 55 mS/cm, about 60 mS/cm, about 65 mS/cm, about 70 mS/cm, about 75 mS/cm, about 80 mS/cm, about 85 mS/cm, about 90 mS/cm, about 95 mS/cm, or about 100 mS/cm. In other aspects of this embodiment, a conductivity gradient has an ending conductivity of, e.g., at least 50 mS/cm, at least 55 mS/cm, at least 60 mS/cm, at least 65 mS/cm, at least 70 mS/cm, at least 75 mS/cm, at least 80 mS/cm, at least 85 mS/cm, at least 90 mS/cm, at least 95 mS/cm, or at least 100 mS/cm. In yet other aspects of this embodiment, a conductivity gradient has an ending conductivity of from, e.g., about 50 mS/cm to about 60 mS/cm, about 50 mS/cm to about 70 mS/cm, about 60 mS/cm to about 70 mS/cm, about 60 mS/cm to about 80 mS/cm, about 70 mS/cm to about 80 mS/cm, about 70 mS/cm to about 90 mS/cm, about 80 mS/cm to about 90 mS/cm, or about 80 mS/cm to about 100 mS/cm.

In aspects of this embodiment, a conductivity gradient has, e.g., a starting conductivity of from between about 1 mS/cm to about 5 mS/cm and an ending conductivity of from between about 50 mS/cm to about 80 mS/cm, a starting conductivity of from between about 2 mS/cm to about 6 mS/cm and an ending conductivity of from between about 55 mS/cm to about 85 mS/cm, a starting conductivity of from between about 3 mS/cm to about 7 mS/cm and an ending conductivity of from between about 55 mS/cm to about 85 mS/cm, a starting conductivity of from between about 4 mS/cm to about 8 mS/cm and an ending conductivity of from between about 55 mS/cm to about 85 mS/cm, a starting conductivity of from between about 5 mS/cm to about 9 mS/cm and an ending conductivity of from between about 60 mS/cm to about 90 mS/cm, a starting conductivity of from between about 6 mS/cm to about 10 mS/cm and an ending conductivity of from between about 60 mS/cm to about 90 mS/cm, a starting conductivity of from between about 7 mS/cm to about 11 mS/cm and an ending conductivity of from between about 65 mS/cm to about 95 mS/cm, a starting conductivity of from between about 8 mS/cm to about 12 mS/cm and an ending conductivity of from between about 65 mS/cm to about 95 mS/cm, or a starting conductivity of from between about 9 mS/cm to about 13 mS/cm and an ending conductivity of from between about 65 mS/cm to about 95 mS/cm.

In other aspects of this embodiment, a conductivity gradient has, e.g., a starting conductivity of from between about 2 mS/cm to about 6 mS/cm and an ending conductivity of from between about 55 mS/cm to about 75 mS/cm, a starting conductivity of from between about 4 mS/cm to about 8 mS/cm and an ending conductivity of from between about 60 mS/cm to about 80 mS/cm, a starting conductivity of from between about 6 mS/cm to about 10 mS/cm and an ending conductivity of from between about 65 mS/cm to about 85 mS/cm, a starting conductivity of from between about 8 mS/cm to about 12 mS/cm and an ending conductivity of from between about 70 mS/cm to about 90 mS/cm, or a starting conductivity of from between about 10 mS/cm to about 14 mS/cm and an ending conductivity of from between about 75 mS/cm to about 95 mS/cm.

In other aspects of this embodiment, a conductivity gradient has, e.g., a starting conductivity of from, e.g., about 4 mS/cm to about 70 mS/cm; about 4 mS/cm to about 80 mS/cm, about 4 mS/cm to about 90 mS/cm, about 6 mS/cm to about 70 mS/cm; about 6 mS/cm to about 80 mS/cm, about 6 mS/cm to about 90 mS/cm, about 8 mS/cm to about 70 mS/cm; about 8 mS/cm to about 80 mS/cm, about 8 mS/cm to about 90 mS/cm, about 10 mS/cm to about 70 mS/cm; about 10 mS/cm to about 80 mS/cm, about 10 mS/cm to about 90 mS/cm, about 12 mS/cm to about 70 mS/cm; about 12 mS/cm to about 80 mS/cm, or about 12 mS/cm to about 90 mS/cm.

A conductivity gradient is established by varying the concentration of electrolytes in a buffered solution as disclosed herein. As used herein, the term "electrolyte" refers to any substance containing free ions that make the substance electrically conductive. The most typical electrolyte is an ionic solution. Non-limiting examples of electrolytes include, e.g., sodium ($Na^+$), potassium ($K^+$), calcium ($Ca^{2+}$), magnesium ($Mg^{2+}$), chloride ($Cl^-$), hydrogen phosphate ($HPO_4^{2-}$), and hydrogen carbonate ($HCO_3^-$).

Electrolyte solutions are normally formed when a salt is placed into a solvent such as water and the individual components dissociate due to the thermodynamic interactions between solvent and solute molecules, in a process called solvation. As used herein, the term "salt" refers to an ionic compound that can result from the neutralization reaction of an acid and a base. A salt is composed of a cation (a positively charged ion) and an anion (a negative ion) so that the product is electrically neutral (without a net charge). These component ions can be inorganic such as chloride ($Cl^-$), as well as organic such as acetate ($CH_3COO^-$) and monatomic ions such as fluoride ($F^-$), as well as polyatomic ions such as sulfate ($SO_4^{2-}$). Molten salts and solutions containing dissolved salts (e.g., sodium chloride in water) are called electrolytes, as they are able to conduct electricity. The salt used to establish a conductivity gradient can be varied as appropriate by one skilled in the art and generally depends, in part, on the protein being eluted and the conductivity values being employed.

There are several varieties of salts. Salts that hydrolyze to produce hydroxide ions when dissolved in water are basic salts and salts that hydrolyze to produce hydronium ions in water are acid salts. Neutral salts are those that are neither acid nor basic salts. Zwitterions contain an anionic center and a cationic center in the same molecule but are not considered to be salts. Common salt-forming cations include, without limitation, Ammonium ($NH_4^+$), Calcium ($Ca^{2+}$), Iron ($Fe^{2+}$ and $Fe^{3+}$), Magnesium ($Mg^{2+}$), Potassium ($K^+$), Pyridinium ($C_5H_5NH^+$), Quaternary Ammonium ($NR_4^+$), and Sodium ($Na^+$). Common salt-forming anions include, without limitation, Acetate ($CH_3COO^-$), Carbonate ($CO_3^{2-}$), Chloride ($Cl^-$), Citrate [($HOC(COO^-)$ or ($CH_2COO^-)2$)], Cyanide ($C\equiv N^-$), Hydroxide ($OH^-$), Nitrate ($NO_3^-$), Nitrite ($NO_2^-$), Oxide ($O_2^-$), Phosphate $PO_4^{3-}$), and Sulfate ($SO_4^{2-}$).

A conductivity gradient may be established by mixing two buffered solutions having the same buffering salt and pH, but different conductivities due to different salt concentrations. Mixing is typically achieved inline by a mixing system comprising two valves, one connected to a vessel containing a buffered solution with a low salt concentration (low conductivity) and the other connected to a vessel containing a buffered solution with a high salt concentration (high conductivity). A conductivity gradient is established by progressively decreasing the proportion of buffered solution with a low concentration of salt while simultaneously increasing the proportion of buffered solution with a high concentration of salt during mixing. In this manner, the salt concentration of the mobile phase increases proportionally thereby establishing a conductivity gradient. Although the proportional increase in the salt concentration is typically linear, and proportional increase based upon a mathematical function can be used with the proviso that the proportional increase is sufficient to elute the protein of interest from the ion exchange resin. Non-limiting examples of a mathematical function include an algebraic function like a linear function, a polynomial function, a nth root function, or a rational function; a transcendental function like an exponential function, a hyperbolic function, or a logarithmic function; a power function; or a periodic function. Although typically established using two buffered solutions, a conductivity gradient may also be established by mixing more than two buffered solutions.

In establishing a conductivity gradient, the starting electrolyte or salt concentration can be any concentration, with the proviso that the concentration establishes a conductivity gradient useful to practice the methods disclosed herein. In aspects of this embodiment, a conductivity gradient has a starting salt concentration of, e.g., about 0 mM, about 0.1 mM, about 0.2 mM, about 0.3 mM, about 0.4 mM, about 0.5 mM, about 0.6 mM, about 0.7 mM, about 0.8 mM, or about 0.9 mM. In other aspects of this embodiment, a conductivity gradient has a starting salt concentration of, e.g., about 1.0 mM, about 2.0 mM, about 3.0 mM, about 4.0 mM, about 5.0 mM, about 6.0 mM, about 7.0 mM, about 8.0 mM, or about 9.0 mM. In yet other aspects of this embodiment, a conductivity gradient has a starting salt concentration of, e.g., about 10 mM, about 20 mM, about 30 mM, about 40 mM, about 50 mM, about 60 mM, about 70 mM, about 80 mM, or about 90 mM.

In aspects of this embodiment, a conductivity gradient has a starting electrolyte or salt concentration of, e.g., at least 0.1 mM, at least 0.2 mM, at least 0.3 mM, at least 0.4 mM, at least 0.5 mM, at least 0.6 mM, at least 0.7 mM, at least 0.8 mM, or at least 0.9 mM. In other aspects of this embodiment, a conductivity gradient has a starting salt concentration of, e.g., at least 1.0 mM, at least 2.0 mM, at least 3.0 mM, at least 4.0 mM, at least 5.0 mM, at least 6.0 mM, at least 7.0 mM, at least 8.0 mM, or at least 9.0 mM. In yet other aspects of this embodiment, a conductivity gradient has a starting salt concentration of, e.g., at least 10 mM, at least 20 mM, at least 30 mM, at least 40 mM, at least 50 mM, at least 60 mM, at least 70 mM, at least 80 mM, or at least 90 mM.

In other aspects of this embodiment, a conductivity gradient has a starting electrolyte or salt concentration of, e.g., at most 0.1 mM, at most 0.2 mM, at most 0.3 mM, at most 0.4 mM, at most 0.5 mM, at most 0.6 mM, at most 0.7 mM, at most 0.8 mM, or at most 0.9 mM. In yet other aspects of this embodiment, a conductivity gradient has a starting salt concentration of, e.g., at most 1.0 mM, at most 2.0 mM, at most 3.0 mM, at most 4.0 mM, at most 5.0 mM, at most 6.0 mM, at most 7.0 mM, at most 8.0 mM, or at most 9.0 mM. In still other aspects of this embodiment, a conductivity gradient has a starting salt concentration of, e.g., at most 10 mM, at most 20 mM, at most 30 mM, at most 40 mM, at most 50 mM, at most 60 mM, at most 70 mM, at most 80 mM, or at most 90 mM.

In yet other aspects of this embodiment, a conductivity gradient has a starting electrolyte or salt concentration of between, e.g., about 0 mM to about 10 mM, about 0 mM to about 50 mM, about 0 mM to about 100 mM, about 0.1 mM to about 10 mM, about 0.1 mM to about 50 mM, about 0.1 mM to about 100 mM, about 1.0 mM to about 10 mM, about 1.0 mM to about 50 mM, about 1.0 mM to about 100 mM, about 10 mM to about 50 mM, or about 10 mM to about 100 mM.

In establishing a conductivity gradient, the final electrolyte or salt concentration can be any concentration, with the proviso that the concentration establishes a conductivity gradient useful to practice the methods disclosed herein. In aspects of this embodiment, a conductivity gradient has a final salt concentration of, e.g., about 100 mM, about 200 mM, about 300 mM, about 400 mM, about 500 mM, about 600 mM, about 700 mM, about 800 mM, about 900 mM, about 1000 mM, about 1100 mM, about 1200 mM, about 1300 mM, about 1400 mM, or about 1500 mM.

In aspects of this embodiment, a conductivity gradient has a final electrolyte or salt concentration of, e.g., at least 100 mM, at least 200 mM, at least 300 mM, at least 400 mM, at least 500 mM, at least 600 mM, at least 700 mM, at least 800 mM, at least 900 mM, at least 1000 mM, at least 1100 mM, at least 1200 mM, at least 1300 mM, at least 1400 mM, or at least 1500 mM.

In other aspects of this embodiment, a conductivity gradient has a final electrolyte or salt concentration of, e.g., at most 100 mM, at most 200 mM, at most 300 mM, at most 400 mM, at most 500 mM, at most 600 mM, at most 700 mM, at most 800 mM, at most 900 mM, at most 1000 mM, at most 1100 mM, at most 1200 mM, at most 1300 mM, at most 1400 mM, or at most 1500 mM.

In yet other aspects of this embodiment, a conductivity gradient has a final electrolyte or salt concentration of between, e.g., about 100 mM to about 500 mM, about 100 mM to about 700 mM, about 100 mM to about 900 mM, about 300 mM to about 500 mM, about 300 mM to about 700 mM, about 300 mM to about 900 mM, about 300 mM to about 1100 mM, about 500 mM to about 700 mM, about 500 mM to about 900 mM, about 500 mM to about 1100 mM, about 500 mM to about 1300 mM, about 700 mM to about 900 mM, about 700 mM to about 1100 mM, about 700 mM to about 1300 mM, about 700 mM to about 1500 mM, about 900 mM to about 1100 mM, about 900 mM to about 1300 mM, or about 900 mM to about 1500 mM.

In still other aspects of this embodiment, a conductivity gradient has, e.g., a starting salt concentration of about 0 mM to about 100 mM and a final salt concentration of about 700 mM to about 1300 mM, a starting salt concentration of about 60 mM to about 80 mM and a final salt concentration of about 900 mM to about 1100 mM, or a starting salt concentration of about 0 mM to about 10 mM and a final salt concentration of about 700 mM to about 800 mM. In further aspects of this embodiment, a conductivity gradient has, e.g., a starting salt concentration of no more than 10 mM and a final salt concentration of at least 700 mM, a starting salt concentration of no more than 50 mM and a final salt concentration of at least 700 mM, a starting salt concentration of no more than 90 mM and a final salt concentration of at least 700 mM, a starting salt concentration of no more than 10 mM and a final salt concentration of at least 900 mM, a starting salt concentration of no more than 50 mM and a final salt concentration of at least 900 mM, a starting salt concentration of no more than 90 mM and a final salt concentration of at least 900 mM, or a starting salt concentration of no more than 10 mM and a final salt concentration of at least 500 mM.

A mobile phase may also comprise a surfactant. Surfactants are compounds that lower the surface tension of a liquid, allowing easier spreading, and lowering of the interfacial tension between two liquids, or between a liquid and a solid. Either a single surfactant may be mixed with the buffered solution disclosed herein, or a plurality of surfactants may be mixed with the buffered solution disclosed herein. Useful surfactants, include, without limitation, ionic surfactants, zwitterionic (amphoteric) surfactants, non-ionic surfactants, or any combination therein. The surfactant used in a method disclosed herein can be varied as appropriate by one skilled in the art and generally depends, in part, on the particular buffer being used, the protein being eluted, and the conductivity values being employed.

Ionic surfactants include anionic surfactants based on permanent (sulfate, sulfonate, phosphate) or pH dependent (carboxylate) anions. Anionic surfactants include, without limitation, alkyl sulfates like ammonium lauryl sulfate and sodium lauryl sulfate (SDS); alkyl ether sulfates like sodium laureth sulfate and sodium myreth sulfate; docusates like dioctyl sodium sulfosuccinate; sulfonate fluorosurfactants like perfluorooctanesulfonate (PFOS) and perfluorobutanesulfonate; alkyl benzene sulfonates; alkyl aryl ether phosphates; alkyl ether phosphates; alkyl carboxylates like fatty acid salts and sodium stearate; sodium lauroyl sarcosinate; and carboxylate fluorosurfactants like perfluorononanoate and perfluorooctanoate.

Ionic surfactants also include cationic surfactants based on permanent or pH dependent cations. Cationic surfactants include, without limitation, alkyltrimethylammonium salts like cetyl trimethylammonium bromide (CTAB) and cetyl trimethylammonium chloride (CTAC); cetylpyridinium chloride (CPC); polyethoxylated tallow amine (POEA); benzalkonium chloride (BAC); benzethonium chloride (BZT); 5-Bromo-5-nitro-1,3-dioxane; dimethyldioctadecylammonium chloride; and dioctadecyldimethylammonium bromide (DODAB), as well as pH-dependent primary, secondary or tertiary amines like surfactants where the primary amines become positively charged at pH greater than 10, or the secondary amines become charged at pH less than 4, like octenidine dihydrochloride.

Zwitterionic surfactants are based on primary, secondary or tertiary amines or quaternary ammonium cation with a sulfonate, a carboxylate, or a phosphate. Zwitterionic surfactants include, without limitation, 3-[(3-Cholamidopropyl)dimethylammonio]-1-propanesulfonate (CHAPS); sultaines like cocamidopropyl hydroxysultaine; betaines like cocamidopropyl betaine; or lecithins.

Non-ionic surfactants are less denaturing and as such are useful to solubilize membrane proteins and lipids while retaining protein-protein interactions. Non-limiting examples of surfactants include polyoxyethylene glycol sorbitan alkyl esters like polysorbate 20 sorbitan monooleate (TWEEN® 20), polysorbate 40 sorbitan monooleate (TWEEN® 40), polysorbate 60 sorbitan monooleate (TWEEN® 60), polysorbate 61 sorbitan monooleate (TWEEN® 61), polysorbate 65 sorbitan monooleate (TWEEN® 65), polysorbate 80 sorbitan monooleate (TWEEN® 80), and polysorbate 81 sorbitan monooleate (TWEEN® 81); poloxamers (polyethylene-polypropylene copolymers), like Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), Poloxamer 407 (PLURONIC® F127); alkyl phenol polyglycol ethers; polyethylene glycol alkyl aryl ethers; polyoxyethylene glycol alkyl ethers, like octaethylene glycol monododecyl ether, pentaethylene glycol monododecyl ether, BRIJ® 30, and BRIJ® 35; 2-dodecoxyethanol (LUBROL®-PX); polyoxyethylene glycol octylphenol ethers like polyoxyethylene (4-5) p-t-octyl phenol (TRITON® X-45) and polyoxyethylene octyl phenyl ether (TRITON® X-100); polyoxyethylene glycol alkylphenol ethers like Nonoxynol-9; phenoxypolyethoxylethanols like nonyl phenoxypolyethoxylethanol and octyl phenoxypolyethoxylethanol; glucoside alkyl ethers like octyl glucopyranoside; maltoside alkyl ethers like dodecyl maltopyranoside; thioglucoside alkyl ethers like heptyl thioglucopyranoside; digitonins; glycerol alkyl esters like glyceryl laurate; alkyl aryl polyether sulfates; alcohol sulfonates; sorbitan alkyl esters; cocamide ethanolamines like cocamide monoethanolamine and cocamide diethanolamine; sucrose monolaurate; dodecyl dimethylamine oxide, and sodium cholate. Other non-limiting examples of surfactants useful in the methods disclosed herein can be found in, e.g., Winslow, et al., *Methods and Compositions for Simultaneously Isolating Hemoglobin from Red Blood Cells and Inactivating Viruses*, U.S. 2008/0138790; Pharmaceutical Dosage Forms and Drug Delivery Systems (Howard C. Ansel et al., eds., Lippincott Williams & Wilkins Publishers, 7$^{th}$ ed. 1999); Remington: The Science and Practice of Pharmacy (Alfonso R. Gennaro ed., Lippincott, Williams & Wilkins, 20$^{th}$ ed. 2000); Goodman & Gilman's The Pharmacological Basis of Therapeutics (Joel G. Hardman et al., eds., McGraw-Hill Professional, 10$^{th}$ ed. 2001); and Handbook of Pharmaceutical Excipients (Raymond C. Rowe et al., APhA Publications, 4$^{th}$ edition 2003), each of which is hereby incorporated by reference in its entirety.

Any concentration of surfactant may be used, with the proviso that the concentration is useful to practice the methods disclosed herein. In aspects of this embodiment, the surfactant is used at a concentration of, e.g., about 0.01% (v/v), about 0.05% (v/v), about 0.075% (v/v), about 0.1% (v/v), about 0.2% (v/v), about 0.3% (v/v), about 0.4% (v/v), about 0.5% (v/v), about 0.6% (v/v), about 0.7% (v/v), about 0.8% (v/v), about 0.9% (v/v), about 1.0% (v/v), about 2.0% (v/v), about 3.0% (v/v), about 4.0% (v/v), about 5.0% (v/v), about 6.0% (v/v), about 7.0% (v/v), about 8.0% (v/v), about 9.0% (v/v), or about 10.0% (v/v). In other aspects of this embodiment, the surfactant is used at a concentration of, e.g., at least 0.01% (v/v), at least 0.05% (v/v), at least 0.075% (v/v), at least 0.1% (v/v), at least 0.25% (v/v), at least 0.5% (v/v), at least 0.75% (v/v), at least 1.0% (v/v), at least 2.5% (v/v), at least 5.0% (v/v), at least 7.5% (v/v), or at least 10.0% (v/v). In yet other aspects of this embodiment, the surfactant is used at a concentration of between, e.g., about 0.1% (v/v) to about 0.5% (v/v), about 0.1% (v/v) to about 1.0% (v/v), about 0.2% (v/v) to about 0.5% (v/v), about 0.2% (v/v) to about 1.0% (v/v), about 0.2% (v/v) to about 2.0% (v/v), about 0.5% (v/v) to about 1.0% (v/v), about 0.5% (v/v) to about 5.0% (v/v), or about 1.0% (v/v) to about 10.0% (v/v).

An elution collection is defined by a conductivity value that starts the collection of eluate from a column and a conductivity value that ends the collection of eluate from the column. The elution collection may be performed as a single eulate collection having a single start and single stop conductivity value, or may comprise a plurality of eluate fractions where each fraction has a start and stop conductivity value. All of the plurality of eluate fractions, or a portion thereof, can be subsequently pooled into a single eluate collection. In aspects of this embodiment, an eulate collection can comprise, e.g., 2 or more eulate fractions, 5 or more eulate fractions, 10 or more eulate fractions, 15 or more eulate fractions, 20 or more eulate fractions, or 25 or more eulate fractions. In other aspects of this embodiment, an eulate collection can comprise, e.g., 2 or more consecutive eulate fractions, 5 or more consecutive eulate fractions, 10 or more eulate consecutive fractions, 15 or more consecutive eulate fractions, 20 or more consecutive eulate fractions, or 25 or more consecutive eulate fractions.

An eluate collection can start when a conductivity value measured for the mobile phase is indicative of a desired amount or activity of a protein being eluted from the ion exchange resin of the stationary phase. The measure of conductivity can occur at any point of the column setup, such as, e.g., any front end point before the mobile phase enters the column, any point within the column, or any back end point after the mobile phase leaves the column. The conductivity can be measured using any sensor that can quantitatively detect conductivity, such as, e.g., a potentiometric sensor, an inductive (or toroidal) sensor, or an amperometric sensor like a current interruption technique (CIT) sensor.

In aspects of this embodiment, an eluate collection can start when a conductivity value measured for the mobile phase is, e.g., about 15.0 mS/cm, about 20.0 mS/cm, about 25.0 mS/cm, about 30.0 mS/cm, or about 35.0 mS/cm. In other aspects of this embodiment, an eluate collection can start when a conductivity value measured for the mobile phase is, e.g., at least 15.0 mS/cm, at least 20.0 mS/cm, at least 25.0 mS/cm, at least 30.0 mS/cm, or at least 35.0 mS/cm. In yet other aspects of this embodiment, an eluate collection can start when a conductivity value measured for the mobile phase is from, e.g., about 15.0 mS/cm to about 25.0 mS/cm, about 15.0 mS/cm to about 30.0 mS/cm, about 15.0 mS/cm to about 35.0 mS/cm, about 20.0 mS/cm to about 30.0 mS/cm, or about 20.0 mS/cm to about 35.0 mS/cm.

In aspects of this embodiment, an eluate collection can start when an inlet conductivity value measured for the mobile phase entering the cation exchange chromatography column is, e.g., about 20.0 mS/cm, about 21.0 mS/cm, about 22.0 mS/cm, about 23.0 mS/cm, about 24.0 mS/cm, about 25.0 mS/cm, about 26.0 mS/cm, about 27.0 mS/cm, about 28.0 mS/cm, about 29.0 mS/cm, about 30.0 mS/cm, about 31.0 mS/cm, about 32.0 mS/cm, about 33.0 mS/cm, about 34.0 mS/cm, or about 35.0 mS/cm. In other aspects of this embodiment, an eluate collection can start when an inlet conductivity value measured for the mobile phase entering the cation exchange chromatography column is, e.g., at least 20.0 mS/cm, at least 21.0 mS/cm, at least 22.0 mS/cm, at least 23.0 mS/cm, at least 24.0 mS/cm, at least 25.0 mS/cm, at least 26.0 mS/cm, at least 27.0 mS/cm, at least 28.0 mS/cm, at least 29.0 mS/cm, a at least bout 30.0 mS/cm, at least 31.0 mS/cm, at least 32.0 mS/cm, at least 33.0 mS/cm, at least 34.0 mS/cm, or at least 35.0 mS/cm. In aspects of this embodiment, an eluate collection can start when an inlet conductivity value measured for the mobile phase entering the cation exchange chromatography column is from, e.g., about 20.0 mS/cm to about 22.0 mS/cm, about 21.0 mS/cm to about 23.0 mS/cm, about 22.0 mS/cm to about 24.0 mS/cm, about 23.0 mS/cm to about 25.0 mS/cm, about 24.0 mS/cm to about 26.0 mS/cm, about 25.0 mS/cm to about 27.0 mS/cm, about 26.0 mS/cm to about 28.0 mS/cm, about 27.0 mS/cm to about 29.0 mS/cm, about 28.0 mS/cm to about 30.0 mS/cm, about 29.0 mS/cm to about 31.0 mS/cm, about 30.0 mS/cm to about 32.0 mS/cm, about 31.0 mS/cm to about 33.0 mS/cm, about 32.0 mS/cm to about 34.0 mS/cm, or about 33.0 mS/cm to about 35.0 mS/cm.

In aspects of this embodiment, an eluate collection can start when an outlet conductivity value measured for the mobile phase leaving the cation exchange chromatography column is, e.g., about 15.0 mS/cm, about 16.0 mS/cm, about 17.0 mS/cm, about 18.0 mS/cm, about 19.0 mS/cm, about 20.0 mS/cm, about 21.0 mS/cm, about 22.0 mS/cm, about 23.0 mS/cm, about 24.0 mS/cm, about 25.0 mS/cm, about 26.0 mS/cm, about 27.0 mS/cm, about 28.0 mS/cm, about 29.0 mS/cm, or about 30.0 mS/cm. In other aspects of this embodiment, an eluate collection can start when an outlet conductivity value measured for the mobile phase leaving the cation exchange chromatography column is, e.g., at least 15.0 mS/cm, at least 16.0 mS/cm, at least 17.0 mS/cm, at least 18.0 mS/cm, at least 19.0 mS/cm, at least 20.0 mS/cm, at least 21.0 mS/cm, at least 22.0 mS/cm, at least 23.0 mS/cm, at least 24.0 mS/cm, at least 25.0 mS/cm, at least 26.0 mS/cm, at least 27.0 mS/cm, at least 28.0 mS/cm, at least 29.0 mS/cm, or at least 30.0 mS/cm. In yet other aspects of this embodiment, an eluate collection can start when an outlet conductivity value measured for the mobile phase leaving the cation exchange chromatography column is, e.g., at most 15.0 mS/cm, at most 16.0 mS/cm, at most 17.0 mS/cm, at most 18.0 mS/cm, at most 19.0 mS/cm, at most 20.0 mS/cm, at most 21.0 mS/cm, at most 22.0 mS/cm, at most 23.0 mS/cm, at most 24.0 mS/cm, at most 25.0 mS/cm, at most 26.0 mS/cm, at most 27.0 mS/cm, at most 28.0 mS/cm, at most 29.0 mS/cm, or at most 30.0 mS/cm. In still other aspects of this embodiment, an eluate collection can start when an outlet conductivity value measured for the mobile phase leaving the cation exchange chromatography column is from, e.g., about 15.0 mS/cm to about 17.0 mS/cm, about 16.0 mS/cm to about 18.0 mS/cm, about 17.0 mS/cm to about 19.0 mS/cm, about 18.0 mS/cm to about 20.0 mS/cm, or about 19.0 mS/cm to about 21.0 mS/cm, about 20.0 mS/cm to about 22.0 mS/cm, about 21.0 mS/cm to about 23.0 mS/cm, about 22.0 mS/cm to about 24.0 mS/cm, about 23.0 mS/cm to about 25.0 mS/cm, about 24.0 mS/cm to about 26.0 mS/cm, about 25.0 mS/cm to about 27.0 mS/cm, about 26.0 mS/cm to about 28.0 mS/cm, about 27.0 mS/cm to about 29.0 mS/cm, or about 28.0 mS/cm to about 30.0 mS/cm.

In aspects of this embodiment, an eluate collection can start when an inlet conductivity value measured for the mobile phase entering the anion exchange chromatography column is, e.g., about 20.0 mS/cm, about 21.0 mS/cm, about 22.0 mS/cm, about 23.0 mS/cm, about 24.0 mS/cm, about 25.0 mS/cm, about 26.0 mS/cm, about 27.0 mS/cm, about 28.0 mS/cm, about 29.0 mS/cm, about 30.0 mS/cm, about 31.0 mS/cm, about 32.0 mS/cm, about 33.0 mS/cm, about 34.0 mS/cm, or about 35.0 mS/cm. In other aspects of this embodiment, an eluate collection can start when an inlet conductivity value measured for the mobile phase entering the anion exchange chromatography column is, e.g., at least 20.0 mS/cm, at least 21.0 mS/cm, at least 22.0 mS/cm, at least 23.0 mS/cm, at least 24.0 mS/cm, at least 25.0 mS/cm, at least 26.0 mS/cm, at least 27.0 mS/cm, at least 28.0 mS/cm, at least 29.0 mS/cm, a at least bout 30.0 mS/cm, at least 31.0 mS/cm, at least 32.0 mS/cm, at least 33.0 mS/cm, at least 34.0 mS/cm, or at least 35.0 mS/cm. In aspects of this embodiment, an eluate collection can start when an inlet conductivity value measured for the mobile phase entering the anion exchange chromatography column is from, e.g., about 20.0 mS/cm to about 22.0 mS/cm, about 21.0 mS/cm to about 23.0 mS/cm, about 22.0 mS/cm to about 24.0 mS/cm, about 23.0 mS/cm to about 25.0 mS/cm, about 24.0 mS/cm to about 26.0 mS/cm, about 25.0 mS/cm to about 27.0 mS/cm, about 26.0 mS/cm to about 28.0 mS/cm, about 27.0 mS/cm to about 29.0 mS/cm, about 28.0 mS/cm to about 30.0 mS/cm, about 29.0 mS/cm to about 31.0 mS/cm, about 30.0 mS/cm to about 32.0 mS/cm, about 31.0 mS/cm to about 33.0 mS/cm, about 32.0 mS/cm to about 34.0 mS/cm, or about 33.0 mS/cm to about 35.0 mS/cm.

In aspects of this embodiment, an eluate collection can start when an outlet conductivity value measured for the mobile phase leaving the anion exchange chromatography column is, e.g., about 15.0 mS/cm, about 16.0 mS/cm, about 17.0 mS/cm, about 18.0 mS/cm, about 19.0 mS/cm, about 20.0 mS/cm, about 21.0 mS/cm, about 22.0 mS/cm, about 23.0 mS/cm, about 24.0 mS/cm, about 25.0 mS/cm, about 26.0 mS/cm, about 27.0 mS/cm, about 28.0 mS/cm, about 29.0 mS/cm, or about 30.0 mS/cm. In other aspects of this embodiment, an eluate collection can start when an outlet conductivity value measured for the mobile phase leaving the anion exchange chromatography column is, e.g., at least 15.0 mS/cm, at least 16.0 mS/cm, at least 17.0 mS/cm, at least 18.0 mS/cm, at least 19.0 mS/cm, at least 20.0 mS/cm, at least 21.0 mS/cm, at least 22.0 mS/cm, at least 23.0 mS/cm, at least 24.0 mS/cm, at least 25.0 mS/cm, at least 26.0 mS/cm, at least 27.0 mS/cm, at least 28.0 mS/cm, at least 29.0 mS/cm, or at least 30.0 mS/cm. In yet other aspects of this embodiment, an eluate collection can start when an outlet conductivity value measured for the mobile phase leaving the anion exchange chromatography column is, e.g., at most 15.0 mS/cm, at most 16.0 mS/cm, at most 17.0 mS/cm, at most 18.0 mS/cm, at most 19.0 mS/cm, at most 20.0 mS/cm, at most 21.0 mS/cm, at most 22.0 mS/cm, at most 23.0 mS/cm, at most 24.0 mS/cm, at most 25.0 mS/cm, at most 26.0 mS/cm, at most 27.0 mS/cm, at most 28.0 mS/cm, at most 29.0 mS/cm, or at most 30.0 mS/cm. In still other aspects of this embodiment, an eluate collection can start when an outlet conductivity value measured for the mobile phase leaving the anion exchange chromatography column is from, e.g., about 15.0 mS/cm to about 17.0 mS/cm, about 16.0 mS/cm to about 18.0 mS/cm, about 17.0 mS/cm to about 19.0 mS/cm, about 18.0 mS/cm to about 20.0 mS/cm, or about 19.0 mS/cm to about 21.0 mS/cm, about 20.0 mS/cm to about 22.0 mS/cm, about 21.0 mS/cm to about 23.0 mS/cm, about 22.0 mS/cm to about 24.0 mS/cm, about 23.0 mS/cm to about 25.0 mS/cm, about 24.0 mS/cm to about 26.0 mS/cm, about 25.0 mS/cm to about 27.0 mS/cm, about 26.0 mS/cm to about 28.0 mS/cm, about 27.0 mS/cm to about 29.0 mS/cm, or about 28.0 mS/cm to about 30.0 mS/cm.

An eluate collection can stop when a conductivity value measured for the mobile phase is indicative of an undesired amount or activity of a protein being eluted from the ion exchange resin of the stationary phase.

In aspects of this embodiment, an eluate collection can stop when a conductivity value measured for the mobile phase is, e.g., about 30.0 mS/cm, about 35.0 mS/cm, about 40.0 mS/cm, about 45.0 mS/cm, about 50.0 mS/cm, about 55.0 mS/cm, or about 60.0 mS/cm. In other aspects of this embodiment, an eluate collection can stop when a conductivity value measured for the mobile phase is, e.g., at least 30.0 mS/cm, at least 35.0 mS/cm, at least 40.0 mS/cm, at least 45.0 mS/cm, at least 50.0 mS/cm, at least 55.0 mS/cm, or at least 60.0 mS/cm. In yet other aspects of this embodiment, an eluate collection can stop when a conductivity value measured for the mobile phase is, e.g., at most 30.0 mS/cm, at most 35.0 mS/cm, at most 40.0 mS/cm, at most 45.0 mS/cm, at most 50.0 mS/cm, at most 55.0 mS/cm, or at most 60.0 mS/cm. In still other aspects of this embodiment, an eluate collection can stop when a conductivity value measured for the mobile phase is from, e.g., about 30.0 mS/cm to about 40.0 mS/cm, about 30.0 mS/cm to about 45.0 mS/cm, about 30.0 mS/cm to about 50.0 mS/cm, about 35.0 mS/cm to about 45.0 mS/cm, about 35.0 mS/cm to about 50.0 mS/cm, or about 35.0 mS/cm to about 60.0 mS/cm.

In aspects of this embodiment, an eluate collection can stop when an inlet conductivity value measured for the mobile phase entering the cation exchange chromatography column is, e.g., about 35.0 mS/cm, about 36.0 mS/cm, about 37.0 mS/cm, about 38.0 mS/cm, about 39.0 mS/cm, about 40.0 mS/cm, about 41.0 mS/cm, about 42.0 mS/cm, about 43.0 mS/cm, about 44.0 mS/cm, about 45.0 mS/cm, about 46.0 mS/cm, about 47.0 mS/cm, about 48.0 mS/cm, about 49.0 mS/cm, or about 50.0 mS/cm. In other aspects of this embodiment, an eluate collection can stop when an inlet conductivity value measured for the mobile phase entering the cation exchange chromatography column is, e.g., at least 35.0 mS/cm, at least 36.0 mS/cm, at least 37.0 mS/cm, at least 38.0 mS/cm, at least 39.0 mS/cm, at least 40.0 mS/cm, at least 41.0 mS/cm, at least 42.0 mS/cm, at least 43.0 mS/cm, at least 44.0 mS/cm, at least 45.0 mS/cm, at least 46.0 mS/cm, at least 47.0 mS/cm, at least 48.0 mS/cm, at least 49.0 mS/cm, or at least 50.0 mS/cm. In yet other aspects of this embodiment, an eluate collection can stop when an inlet conductivity value measured for the mobile phase entering the cation exchange chromatography column is, e.g., at most 35.0 mS/cm, at most 36.0 mS/cm, at most 37.0 mS/cm, at most 38.0 mS/cm, at most 39.0 mS/cm, at most 40.0 mS/cm, at most 41.0 mS/cm, at most 42.0 mS/cm, at most 43.0 mS/cm, at most 44.0 mS/cm, at most 45.0 mS/cm, at most 46.0 mS/cm, at most 47.0 mS/cm, at most 48.0 mS/cm, at most 49.0 mS/cm, or at most 50.0 mS/cm. In still other aspects of this embodiment, an eluate collection can stop when an inlet conductivity value measured for the mobile phase entering the cation exchange chromatography column is from, e.g., about 35.0 mS/cm to about 37.0 mS/cm, about 36.0 mS/cm to about 38.0 mS/cm, about 37.0 mS/cm to about 39.0 mS/cm, about 38.0 mS/cm to about 40.0 mS/cm, about 39.0 mS/cm to about 41.0 mS/cm, about 40.0 mS/cm to about 42.0 mS/cm, about 41.0 mS/cm to about 43.0 mS/cm, about 42.0 mS/cm to about 44.0 mS/cm, about 43.0 mS/cm to about 45.0 mS/cm, about 44.0 mS/cm to about 46.0 mS/cm, about 45.0 mS/cm to about 47.0 mS/cm, about 46.0 mS/cm to about 48.0 mS/cm, about 47.0 mS/cm to about 49.0 mS/cm, or about 48.0 mS/cm to about 50.0 mS/cm.

In aspects of this embodiment, an eluate collection can stop when an outlet conductivity value measured for the mobile phase leaving the cation exchange chromatography column is, e.g., about 30.0 mS/cm, about 31.0 mS/cm, about 32.0 mS/cm, about 33.0 mS/cm, about 34.0 mS/cm, about 35.0 mS/cm, about 36.0 mS/cm, about 37.0 mS/cm, about 38.0 mS/cm, about 39.0 mS/cm, about 40.0 mS/cm, about 41.0 mS/cm, or about 42.0 mS/cm. In other aspects of this embodiment, an eluate collection can stop when an outlet conductivity value measured for the mobile phase leaving the cation exchange chromatography column is, e.g., at least 30.0 mS/cm, at least 31.0 mS/cm, at least 32.0 mS/cm, at least 33.0 mS/cm, at least 34.0 mS/cm, at least 35.0 mS/cm, at least 36.0 mS/cm, at least 37.0 mS/cm, at least 38.0 mS/cm, at least 39.0 mS/cm, at least 40.0 mS/cm, at least 41.0 mS/cm, or at least 42.0 mS/cm. In yet other aspects of this embodiment, an eluate collection can stop when an outlet conductivity value measured for the mobile phase leaving the cation exchange chromatography column is, e.g., at most 30.0 mS/cm, at most 31.0 mS/cm, at most 32.0 mS/cm, at most 33.0 mS/cm, at most 34.0 mS/cm, at most 35.0 mS/cm, at most 36.0 mS/cm, at most 37.0 mS/cm, at most 38.0 mS/cm, at most 39.0 mS/cm, at most 40.0 mS/cm, at most 41.0 mS/cm, or at most 42.0 mS/cm. In still other aspects of this embodiment, an eluate collection can stop when an outlet conductivity value measured for the mobile phase leaving the cation exchange chromatography column is from, e.g., about 30.0 mS/cm to about 32.0 mS/cm, about 31.0 mS/cm to about 33.0 mS/cm, about 32.0 mS/cm to about 34.0 mS/cm, about 33.0 mS/cm to about 35.0 mS/cm, about 34.0 mS/cm to about 36.0 mS/cm, about 35.0 mS/cm to about 37.0 mS/cm, about 36.0 mS/cm to about 38.0 mS/cm, about 37.0 mS/cm to about 39.0 mS/cm, about 38.0 mS/cm to about 40.0 mS/cm, about 39.0 mS/cm to about 41.0 mS/cm, or about 40.0 mS/cm to about 42.0 mS/cm.

In aspects of this embodiment, an eluate collection can stop when an inlet conductivity value measured for the mobile phase entering the anion exchange chromatography column is, e.g., about 45.0 mS/cm, about 46.0 mS/cm, about 47.0 mS/cm, about 48.0 mS/cm, about 49.0 mS/cm, about 50.0 mS/cm, about 51.0 mS/cm, about 52.0 mS/cm, about 53.0 mS/cm, about 54.0 mS/cm, about 55.0 mS/cm, about 56.0 mS/cm, about 57.0 mS/cm, or about 58.0 mS/cm. In other aspects of this embodiment, an eluate collection can stop when an inlet conductivity value measured for the mobile phase entering the anion exchange chromatography column is, e.g., at least 45.0 mS/cm, at least 46.0 mS/cm, at least 47.0 mS/cm, at least 48.0 mS/cm, at least 49.0 mS/cm, at least 50.0 mS/cm, at least 51.0 mS/cm, at least 52.0 mS/cm, at least 53.0 mS/cm, at least 54.0 mS/cm, at least 55.0 mS/cm, at least 56.0 mS/cm, at least 57.0 mS/cm, or at least 58.0 mS/cm. In yet other aspects of this embodiment, an eluate collection can stop when an inlet conductivity value measured for the mobile phase entering the anion exchange chromatography column is, e.g., at most 45.0 mS/cm, at most 46.0 mS/cm, at most 47.0 mS/cm, at most 48.0 mS/cm, at most 49.0 mS/cm, at most 50.0 mS/cm, at most 51.0 mS/cm, at most 52.0 mS/cm, at most 53.0 mS/cm, at most 54.0 mS/cm, at most 55.0 mS/cm, at most 56.0 mS/cm, at most 57.0 mS/cm, or at most 58.0 mS/cm. In still other aspects of this embodiment, an eluate collection can stop when an inlet conductivity value measured for the mobile phase entering the anion exchange chromatography column is from, e.g., about 45.0 mS/cm to about 47.0 mS/cm, about 46.0 mS/cm to about 48.0 mS/cm, about 47.0 mS/cm to about 49.0 mS/cm, about 48.0 mS/cm to about 50.0 mS/cm, about 49.0 mS/cm to about 51.0 mS/cm, about 50.0 mS/cm to about 52.0 mS/cm, about 51.0 mS/cm to about 53.0 mS/cm, about 52.0 mS/cm to about 54.0 mS/cm, about 53.0 mS/cm to about 55.0 mS/cm, about 54.0 mS/cm to about 56.0 mS/cm, about 55.0 mS/cm to about 57.0 mS/cm, or about 56.0 mS/cm to about 58.0 mS/cm.

In aspects of this embodiment, an eluate collection can stop when an outlet conductivity value measured for the mobile phase leaving the anion exchange chromatography column is, e.g., about 40.0 mS/cm, about 41.0 mS/cm, about 42.0 mS/cm, about 43.0 mS/cm, about 44.0 mS/cm, about 45.0 mS/cm, about 46.0 mS/cm, about 47.0 mS/cm, about 48.0 mS/cm, about 49.0 mS/cm, about 50.0 mS/cm, about 51.0 mS/cm, about 52.0 mS/cm, or about 53.0 mS/cm. In other aspects of this embodiment, an eluate collection can stop when an outlet conductivity value measured for the mobile phase leaving the anion exchange chromatography column is, e.g., at least 40.0 mS/cm, at least 41.0 mS/cm, at least 42.0 mS/cm, at least 43.0 mS/cm, at least 44.0 mS/cm, at least 45.0 mS/cm, at least 46.0 mS/cm, at least 47.0 mS/cm, at least 48.0 mS/cm, at least 49.0 mS/cm, at least 50.0 mS/cm, at least 51.0 mS/cm, at least 52.0 mS/cm, or at least 53.0 mS/cm. In yet other aspects of this embodiment, an eluate collection can stop when an outlet conductivity value measured for the mobile phase leaving the anion exchange chromatography column is, e.g., at most 40.0 mS/cm, at most 41.0 mS/cm, at most 42.0 mS/cm, at most 43.0 mS/cm, at most 44.0 mS/cm, at most 45.0 mS/cm, at most 46.0 mS/cm, at most 47.0 mS/cm, at most 48.0 mS/cm, at most 49.0 mS/cm, at most 50.0 mS/cm, at most 51.0 mS/cm, at most 52.0 mS/cm, or at most 53.0 mS/cm. In still other aspects of this embodiment, an eluate collection can stop when an outlet conductivity value measured for the mobile phase leaving the anion exchange chromatography column is from, e.g., about 40.0 mS/cm to about 42.0 mS/cm, about 41.0 mS/cm to about 43.0 mS/cm, about 42.0 mS/cm to about 44.0 mS/cm, about 43.0 mS/cm to about 45.0 mS/cm, about 44.0 mS/cm to about 46.0 mS/cm, about 45.0 mS/cm to about 47.0 mS/cm, about 46.0 mS/cm to about 48.0 mS/cm, about 47.0 mS/cm to about 49.0 mS/cm, about 48.0 mS/cm to about 50.0 mS/cm, about 49.0 mS/cm to about 51.0 mS/cm, about 50.0 mS/cm to about 52.0 mS/cm, or about 51.0 mS/cm to about 53.0 mS/cm.

In another aspects of this embodiment, an eluate collection can start when an inlet conductivity value measured for the mobile phase entering the cation exchange chromatography column is from about 25.0 mS/cm to about 27.0 mS/cm and stops when the inlet conductivity value measured for the mobile phase entering the cation exchange chromatography column is from about 41.0 mS/cm to about 43.0 mS/cm. In yet another aspects of this embodiment, an eluate collection can start when an inlet conductivity value measured for the mobile phase entering the cation exchange chromatography column is from about 25.0 mS/cm to about 27.0 mS/cm and stops when the inlet conductivity value measured for the mobile phase entering the cation exchange chromatography column is from about 41.0 mS/cm to about 43.0 mS/cm, and wherein the conductivity gradient is from about 8 mS/cm to about 90 mS/cm. In still another aspects of this embodiment, an eluate collection can start when an inlet conductivity value measured for the mobile phase entering the cation exchange chromatography column is from about 25.0 mS/cm to about 27.0 mS/cm and stops when the inlet conductivity value measured for the mobile phase entering the cation exchange chromatography column is from about 41.0 mS/cm to about 43.0 mS/cm, wherein the conductivity gradient is from about 8 mS/cm to about 90 mS/cm and the protein being eluted is Factor VIII.

In another aspects of this embodiment, an eluate collection can start when an outlet conductivity value measured for the mobile phase exiting the cation exchange chromatography column is from about 19.0 mS/cm about 21.0 mS/cm and stop when the outlet conductivity value measured for the mobile phase exiting the cation exchange chromatography column is from about 34.5 mS/cm to about 36.5 mS/cm. In yet another aspects of this embodiment, an eluate collection can start when an outlet conductivity value measured for the mobile phase exiting the cation exchange chromatography column is from about 19.0 mS/cm about 21.0 mS/cm and stop when the outlet conductivity value measured for the mobile phase exiting the cation exchange chromatography column is from about 34.5 mS/cm to about 36.5 mS/cm, and wherein the conductivity gradient is from about 8 mS/cm to about 90 mS/cm. In still another aspects of this embodiment, an eluate collection can start when an outlet conductivity value measured for the mobile phase exiting the cation exchange chromatography column is from about 19.0 mS/cm about 21.0 mS/cm and can stop when the outlet conductivity value measured for the mobile phase exiting the cation exchange chromatography column is from about 34.5 mS/cm to about 36.5 mS/cm, wherein the conductivity gradient is from about 8 mS/cm to about 90 mS/cm and the protein being eluted is Factor VIII.

In another aspects of this embodiment, an eluate collection can start when an inlet conductivity value measured for the mobile phase entering the anion exchange chromatography column is from about 27.8 mS/cm to about 29.8 mS/cm and stop when the inlet conductivity value measured for the mobile phase entering the anion exchange chromatography column is from about 51.0 mS/cm to about 53.0 mS/cm. In yet another aspects of this embodiment, an eluate collection can start when an inlet conductivity value measured for the mobile phase entering the anion exchange chromatography column is from about 27.8 mS/cm to about 29.8 mS/cm and stop when the inlet conductivity value measured for the mobile phase entering the anion exchange chromatography column is from about 51.0 mS/cm to about 53.0 mS/cm, and wherein the conductivity gradient is from about 4 mS/cm to about 80 mS/cm. In still another aspects of this embodiment, an eluate collection can start when an inlet conductivity value measured for the mobile phase entering the anion exchange chromatography column is from about 27.8 mS/cm to about 29.8 mS/cm and stop when the inlet conductivity value measured for the mobile phase entering the anion exchange chromatography column is from about 51.0 mS/cm to about 53.0 mS/cm, wherein the conductivity gradient is from about 4 mS/cm to about 80 mS/cm and the protein being eluted is Factor VIII.

In another aspects of this embodiment, an eluate collection can start when an outlet conductivity value measured for the mobile phase exiting the anion exchange chromatography column is from about 21.0 mS/cm to about 23.0 mS/cm and stop when the outlet conductivity value measured for the mobile phase exiting the anion exchange chromatography column is from about 45.5 mS/cm to about 47.5 mS/cm. In yet another aspects of this embodiment, an eluate collection can start when an outlet conductivity value measured for the mobile phase exiting the anion exchange chromatography column is from about 21.0 mS/cm to about 23.0 mS/cm and stop when the outlet conductivity value measured for the mobile phase exiting the anion exchange chromatography column is from about 45.5 mS/cm to about 47.5 mS/cm, and wherein the conductivity gradient is from about 4 mS/cm to about 80 mS/cm. In still another aspects of this embodiment, an eluate collection can start when an outlet conductivity value measured for the mobile phase exiting the anion exchange chromatography column is from about 21.0 mS/cm to about 23.0 mS/cm and stop when the outlet conductivity value measured for the mobile phase exiting the anion exchange chromatography column is from about 45.5 mS/cm to about 47.5 mS/cm, wherein the conductivity gradient is from about 4 mS/cm to about 80 mS/cm and the protein being eluted is Factor VIII.

Aspects of the present specification disclose, in part, a protein to be retained by the column, and an eluate collection comprising a desired amount or activity of a protein. A protein disclosed herein can be a blood protein such as, e.g., a blood coagulation protein, albumin, and/or an immunoglobulin. Non-limiting examples of a blood protein include ADAMTS-13, α1-antiplasmin, α2-antiplasmin, antithrombin, antithrombin III, cancer procoagulant, erythropoietin, Factor II, Factor V, Factor VI, Factor VII, Factor VIII, Factor IX, Factor X, Factor XI, Factor XII, Factor XIII, fibronectin, fibrinogen, heparin cofactor II, high-molecular-weight kininogen, intramuscular immunoglobulin, intravenous immunoglobulin, plasminogen, plasminogen activator inhibitor-1, plasminogen activator inhibitor-2, prekallikrein, protein C, protein S, protein Z, protein Z-related protease inhibitor, tissue factor, tissue plasminogen activator, urokinase, or Von Willebrand Factor.

A protein disclosed herein may be obtained from an organism that naturally expresses the protein, from a transgenic organism genetically-engineered to express the protein, or from a cell line recombinantly producing the protein. Non-limiting examples of an organism include birds and mammals, such as, e.g., mice, rats, goats, sheep, horses, donkeys, cows, primates and humans. Non-limiting examples of a transgenic organisms include organisms disclosed herein that have been genetically-engineered to express a protein of interest. A protein disclosed herein from an organism or transgenic organism may be obtained from a biological fluid, tissue or organ extract, or other source from an organism using routine methods known in the art. For example, to obtain a blood protein whole blood from an organism or transgenic organism can be drawn in a serum separator tube. The blood is allowed to clot and the clotted blood centrifuged to pellet the debris. The resulting serum sample (i.e., the supernatant) can then be aliquoted and/or stored at −20° C. until needed. Non-limiting examples of specific protocols for blood collection and serum preparation are described in, e.g., Di Lorenzo and Strasinger, BLOOD COLLECTION IN HEALTHCARE (F.A. Davis Company, 2001); and Diana Garza & Kathleen Becan-McBride, PHLEBOTOMY HANDBOOK: BLOOD COLLECTION ESSENTIALS (Prentice Hall, 6$^{th}$ ed., 2002).

Alternatively, various prokaryote and/or eukaryotic expression systems may also be employed to recombinantly express a protein disclosed herein. Expression systems can include any of a variety of characteristics including, without limitation, inducible expression, non-inducible expression, constitutive expression, tissue-specific expression, cell-specific expression, viral-mediated expression, stably-integrated expression, and transient expression. How to make and use such expression systems are known in the art.

Generally, a polynucleotide encoding the polypeptide of interest is cloned into an expression vector. Prokaryote expression vectors typically comprise an origin of replication, a suitable promoter and/or enhancer elements, and also sites necessary ribosome binding, polyadenylation, transcriptional termination, as well as 5' flanking non-transcribed sequences and other non-transcribed genetic elements. Exemplary prokaryotic vectors include pET and pRSET using promoters such as, e.g., a bacteriophage T7 promoter. Eukaryotic expression vectors typically comprise an origin of replication, a suitable promoter and/or enhancer elements, and also sites necessary ribosome binding, polyadenylation, splicing, transcriptional termination, as well as 5' flanking non-transcribed sequences and other non-transcribed genetic elements. Exemplary yeast vectors include pAO, pMET, pPIC, pPICZ, and pYES using promoters such as, e.g., AOX1, AUG1, GAP, and GAL1. Exemplary insect vectors include pAc5, pBAC, pIB, pMIB, pMT using promoters such as, e.g., PH, p10, MT, Ac5, OpIE2, gp64, and polh. Exemplary mammalian vectors include pBPV, pCMV, pCMVTNT, pDNA, pDisplay, pMSG, pOG44, pQBI25, pRc/RSV, pSECTag, pSECTag2, pSG, pSV2cat, pSVK3, pSVL, pUCIG-MET, pVAX1, pWLneo, and pXT1 using promoters such as, e.g., beta-casein, beta-lactoglobulin, whey acid promoter, HSV thymidine kinase, early and late simian virus 40 (SV40), LTRs from retrovirus, and mouse metallothionein-1. Selectable markers include Ampicillin, Chloramphenicol transferase, Kanamycin, Neomycin, and Tetracycline. Suitable expression vectors are known in the art and commercially available.

Cell capable of expressing a compatible vector include prokaryotic cells, eukaryotic cells, and cell lines derived from prokaryotic and eukaryotic cells. Non-limiting examples of prokaryotic strains include those derived from, e.g., *Escherichia coli, Bacillus subtilis, Bacillus licheniformis, Bacteroides fragilis, Clostridia perfringens, Clostridia difficle, Caulobacter crescentus, Lactococcus lactis, Methylobacterium extorquens, Neisseria meningirulls, Neisseria meningitidis, Pseudomonas fluorescens* and *Salmonella typhimurium*. Non-limiting examples of yeast strains include those derived from, e.g., *Pichia pastoris, Pichia methanolica, Pichia angusta, Schizosaccharomyces pombe, Saccharomyces cerevisiae* and *Yarrowia lipolytica*. Plant cells and cell lines derived from plants include cells from, e.g., species of monocots, such as, e.g., *Zea mays* and species of dicots, such as, e.g., *Arabidopsis thaliana, Triticum aestivum, Lemna gibba* and *Lemna minor*. Insect cells and cell lines derived from insects include cells from, e.g., *Spodoptera frugiperda, Trichoplusia ni, Drosophila melanogaster* and *Manduca sexta*. Non-limiting examples of insect cell lines include High-Five, $K_c$, Schneider's Drosophila line 2 (S2), SF9, and SF21 cell lines. Mammalian cells and cell lines derived from mammalian cells include cells from, e.g., mouse, rat, hamster, porcine, bovine, equine, primate and human. Non-limiting examples of mammalian cell lines include 1A3, 3T3, 6E6, 10T1/2, APRT, BALB/3T3, BE (2)-C, BHK, BT, C6, C127, CHO, CHP3, COS-1, COS-7, CPAE, ESK-4, FB2, GH1, GH3, HeLa, HEK-293, HepG2, HL-60, IMR-32, L2, LLC-PK1, L-M, MCF-7, NB4, NBL-6, NCTC, Neuro 2A, NIE-115, NG108-15, NIH3T3, PC12, PK15, SBAC, SH-SY5Y, SK-Hep, SK-N-DZ, SK-N-F1, SK-N-SH, ST, SW-13, and VV-1 cell lines. Cell lines may be obtained from the American Type Culture Collection, European Collection of Cell Cultures and/or the German Collection of Microorganisms and Cell Cultures.

In aspects of this embodiment, an eluate collection comprises, e.g., at least 25%, at least 30%, at least 40%, at least 50%, at least 60%, at least 70%, at least 75%, at least 80%, at least 85%, at least 90%, or at least 95% of the protein retained by an ion exchange chromatography column before an elution collection started. In other aspects of this embodiment, an eluate collection comprises between, e.g., about 25% to about 100%, about 30% to about 100%, about 40% to about 100%, about 50% to about 100%, about 60% to about 100%, about 70% to about 100%, about 75% to about 100%, about 80% to about 100%, about 85% to about 100%, about 90% to about 100%, about 25% to about 95%, about 30% to about 95%, about 40% to about 95%, about 50% to about 95%, about 60% to about 95%, about 70% to about 95%, about 75% to about 95%, about 80% to about 95%, about 85% to about 95%, about 90% to about 95%, about 25% to about 90%, about 30% to about 90%, about 40% to about 90%, about 50% to about 90%, about 60% to about 90%, about 70% to about 90%, about 75% to about 90%, about 80% to about 90%, or about 85% to about 90% of the protein retained by an ion exchange chromatography column before an elution collection started.

In aspects of this embodiment, an eluate collection comprises, e.g., at least 25%, at least 30%, at least 40%, at least 50%, at least 60%, at least 70%, at least 75%, at least 80%, at least 85%, at least 90%, or at least 95% of the protein amount retained by an ion exchange chromatography column before an elution collection started. In other aspects of this embodiment, an eluate collection comprises between, e.g., about 25% to about 100%, about 30% to about 100%, about 40% to about 100%, about 50% to about 100%, about 60% to about 100%, about 70% to about 100%, about 75% to about 100%, about 80% to about 100%, about 85% to about 100%, about 90% to about 100%, about 25% to about 95%, about 30% to about 95%, about 40% to about 95%, about 50% to about 95%, about 60% to about 95%, about 70% to about 95%, about 75% to about 95%, about 80% to about 95%, about 85% to about 95%, about 90% to about 95%, about 25% to about 90%, about 30% to about 90%, about 40% to about 90%, about 50% to about 90%, about 60% to about 90%, about 70% to about 90%, about 75% to about 90%, about 80% to about 90%, or about 85% to about 90% of the protein amount retained by an ion exchange chromatography column before an elution collection started.

In aspects of this embodiment, an eluate collection comprises, e.g., at least 25%, at least 30%, at least 40%, at least 50%, at least 60%, at least 70%, at least 75%, at least 80%, at least 85%, at least 90%, or at least 95% of the protein activity retained by an ion exchange chromatography column before an elution collection started. In other aspects of this embodiment, an eluate collection comprises between, e.g., about 25% to about 100%, about 30% to about 100%, about 40% to about 100%, about 50% to about 100%, about 60% to about 100%, about 70% to about 100%, about 75% to about 100%, about 80% to about 100%, about 85% to about 100%, about 90% to about 100%, about 25% to about 95%, about 30% to about 95%, about 40% to about 95%, about 50% to about 95%, about 60% to about 95%, about 70% to about 95%, about 75% to about 95%, about 80% to about 95%, about 85% to about 95%, about 90% to about 95%, about 25% to about 90%, about 30% to about 90%, about 40% to about 90%, about 50% to about 90%, about 60% to about 90%, about 70% to about 90%, about 75% to about 90%, about 80% to about 90%, or about 85% to about 90% of the protein activity retained by an ion exchange chromatography column before an elution collection started.

Detecting an activity of a protein can be accomplished by any assay that can qualitatively or quantitatively measure a characteristic indicative of an activity associated with the protein being monitored, including, without limitation, a non-specific protein assay, such as, e.g., UV absorption or a chemical-based assay like a Bradford assay; or a specific protein assay, such as, e.g., an in vitro assay, a cell-based assay, or an in vivo assay. The actual assay used to detect an activity of a protein as disclosed herein can be determined by a person of ordinary skill in the art by taking into account factors, including, without limitation, the protein being assayed, the amount of protein present in the fluid, the characteristic being assayed, and the preference of the person of ordinary skill in the art.

For example, a chromogenic assay based on the blood coagulation cascade can be used to detect FVIII activity. In this assay, thrombin activated Factor VIII forms a complex with Factor IXa, and this complex subsequently activates Factor X. Activated Factor X activity can be accessed by the hydrolysis of a chromogenic substrate which liberates a chromogenic group like p-nitro-aniline (pNA). The initial rate of pNA release, as determined by a change in absorbance per minute measured at 405 nm in OD, is proportional to the Factor Xa activity and subsequently to the FVIII activity in the sample. By using excess of Factor IXa, and Factor X, the rate of activation of Factor X is solely proportional to the amount of thrombin cleaved Factor VIII present in the sample. Alternatively, Factor IXa activity can be determined by altering conditions so that Factor VIII and Factor X are in excess, and as such, Factor IXa is rate limiting. Similarly, Factor X activity can be determined by altering conditions so that Factor VIII and Factor IXa are in excess, and as such, Factor X is rate limiting. Thus, Factor VIII activity, as well as Factor IXa and Factor X, can be detected using a chromogenic assay based on the blood coagulation cascade.

As another example, a one-stage clotting assay that applies the Partial Activated Partial Thromboplastin Time (APTT) can be used to detect FVIII activity. In this assay, samples comprising Factor VIII, along with $CaCl_2$, are added to Factor VIII deficient plasma in order to promote coagulation and the effect of this sample on APTT clotting time of the plasma is a measure of the Factor VIII activity. Activities of unknown samples are calculated by comparing the Factor VIII activity observed with a standard curve generated from known Factor VIII activity samples. This blood clotting assay may also be used for any other protein involved in the blood coagulation cascade by using a plasma deficient in the protein being assayed.

Aspects of the present specification disclose, in part, a closed system. The elution method disclosed herein is considered a closed system because it may be fully automated and does not require operator participation in terms of collecting an elution fraction or multiple elution fractions, assaying fraction(s) for protein content, identify fraction(s) containing a threshold amount of the polypeptide of interest, and pooling of fractions for subsequent processing. As such, the elution method disclosed herein reduces the amount of operator labor in terms of supervising the collection process to prevent mechanical incident and decreases the likelihood of operator error regarding the calculation of the fractions to be pooled or during the manual pooling itself.

Aspects of the present specification can also be described as follows:

1. A method of collecting an elution from a column, the method comprising the steps of: a) applying a sample comprising a protein to a cation exchange chromatography column, wherein the application causes the protein to be retained by the column; b) applying a mobile phase to the cation exchange chromatography column, the mobile phase comprising a buffered solution, wherein application of the mobile phase establishes a conductivity gradient of from about 8 mS/cm to about 90 mS/cm; c) starting an eluate collection when an inlet conductivity value measured for the mobile phase entering the cation exchange chromatography column is from about 25.0 mS/cm to about 27.0 mS/cm; and d) stopping the eluate collection when the inlet conductivity value measured for the mobile phase entering the cation exchange chromatography column is from about 41.0 mS/cm to about 43.0 mS/cm; wherein the eluate collection comprises at least 25% of the protein retained by the cation exchange chromatography column in step (a).

2. A method of collecting an elution from a column, the method comprising the steps of: a) applying a sample comprising a protein to a cation exchange chromatography column, wherein the application causes the protein to be retained by the column; b) applying a mobile phase to the cation exchange chromatography column, the mobile phase comprising a buffered solution, wherein application of the mobile phase establishes a conductivity gradient of from about 8 mS/cm to about 90 mS/cm; c) starting an eluate collection when an outlet conductivity value measured for the mobile phase exiting the cation exchange chromatography column is from about 19.0 mS/cm about 21.0 mS/cm; and d) stopping the eluate collection when the outlet conductivity value measured for the mobile phase exiting the cation exchange chromatography column is from about 34.5 mS/cm to about 36.5 mS/cm; wherein the eluate collection comprises at least 25% of the protein retained by the cation exchange chromatography column in step (a).

3. A method of collecting an elution from a column, the method comprising the steps of: a) applying a sample comprising a protein to a cation exchange chromatography column, wherein the application causes the protein to be retained by the column; b) applying a mobile phase to the cation exchange chromatography column, the mobile phase comprising a buffered solution, wherein application of the mobile phase establishes a conductivity gradient of from about 8 mS/cm to about 90 mS/cm; c) starting an eluate collection when an inlet conductivity value measured for the mobile phase entering the cation exchange chromatography column is from about 25.0 mS/cm to about 27.0 mS/cm or an outlet conductivity value measured for the mobile phase exiting the cation exchange chromatography column is from about 19.0 mS/cm about 21.0 mS/cm; and d) stopping the eluate collection when the inlet conductivity value measured for the mobile phase entering the cation exchange chromatography column is from about 41.0 mS/cm to about 43.0 mS/cm or the outlet conductivity value measured for the mobile phase exiting the cation exchange chromatography column is from about 34.5 mS/cm to about 36.5 mS/cm; wherein the eluate collection comprises at least 25% of the protein retained by the cation exchange chromatography column in step (a).

4. A method of collecting an elution from a column, the method comprising the steps of: a) applying a sample comprising a protein to a cation exchange chromatography column, wherein the application causes the protein to be retained by the column; b) applying a mobile phase to the cation exchange chromatography column, the mobile phase comprising a buffered solution, wherein application of the mobile phase establishes a conductivity gradient of from about 8 mS/cm to about 90 mS/cm; c) starting an eluate collection when an inlet conductivity value measured for the mobile phase entering the cation exchange chromatography column is at least 21 mS/cm; and d) stopping the eluate collection when the inlet conductivity value measured for the mobile phase entering the cation exchange chromatography column is at most 47 mS/cm; wherein the eluate collection comprises at least 25% of the protein retained by the cation exchange chromatography column in step (a).

5. A method of collecting an elution from a column, the method comprising the steps of: a) applying a sample comprising a protein to a cation exchange chromatography column, wherein the application causes the protein to be retained by the column; b) applying a mobile phase to the cation exchange chromatography column, the mobile phase comprising a buffered solution, wherein application of the mobile phase establishes a conductivity gradient of from about 8 mS/cm to about 90 mS/cm; c) starting an eluate collection when an outlet conductivity value measured for the mobile phase exiting the cation exchange chromatography column is at least about 15.0 mS/cm; and d) stopping the eluate collection when the outlet conductivity value measured for the mobile phase exiting the cation exchange chromatography column is at most 41 mS/cm; wherein the eluate collection comprises at least 25% of the protein retained by the cation exchange chromatography column in step (a).

6. A method of collecting an elution from a column, the method comprising the steps of: a) applying a sample comprising a protein to a cation exchange chromatography column, wherein the application causes the protein to be retained by the column; b) applying a mobile phase to the cation exchange chromatography column, the mobile phase comprising a buffered solution, wherein application of the mobile phase establishes a conductivity gradient of from about 8 mS/cm to about 90 mS/cm; c) starting an eluate collection when an inlet conductivity value measured for the mobile phase entering the cation exchange chromatography column is at least 21 mS/cm or an outlet conductivity value measured for the mobile phase exiting the cation exchange chromatography column is at least 15 mS/cm; and d) stopping the eluate collection when the inlet conductivity value measured for the mobile phase entering the cation exchange chromatography column is at most 47 mS/cm or the outlet conductivity value measured for the mobile phase exiting the cation exchange chromatography column is at most 41 mS/cm; wherein the eluate collection comprises at least 25% of the protein retained by the cation exchange chromatography column in step (a).

7. The embodiments of 1-6, wherein the eluate collection comprises at least 50% of the protein retained by the cation exchange chromatography column in step (a), or at least 75% of the protein retained by the cation exchange chromatography column in step (a).

8. The embodiments of 1-7, wherein the protein retained by the cation exchange chromatography column is measured by amount or an activity.

9. A method of collecting an elution from a column, the method comprising the steps of: a) applying a sample comprising a Factor VIII to a cation exchange chromatography column, wherein the application causes the Factor VIII to be retained by the column; b) applying a mobile phase to the cation exchange chromatography column, the mobile phase comprising a buffered solution, wherein application of the mobile phase establishes a conductivity gradient of from about 8 mS/cm to about 90 mS/cm; c) starting an eluate collection when an inlet conductivity value measured for the mobile phase entering the cation exchange chromatography column is from about 25.0 mS/cm to about 27.0 mS/cm; and d) stopping the eluate collection when the inlet conductivity value measured for the mobile phase entering the cation exchange chromatography column is from about 41.0 mS/cm to about 43.0 mS/cm; wherein the eluate collection comprises at least 25% of the Factor VIII retained by the cation exchange chromatography column in step (a).

10. A method of collecting an elution from a column, the method comprising the steps of: a) applying a sample comprising a Factor VIII to a cation exchange chromatography column, wherein the application causes the Factor VIII to be retained by the column; b) applying a mobile phase to the cation exchange chromatography column, the mobile phase comprising a buffered solution, wherein application of the mobile phase establishes a conductivity gradient of from about 8 mS/cm to about 90 mS/cm; c) starting an eluate collection when an outlet conductivity value measured for the mobile phase exiting the cation exchange chromatography column is from about 19.0 mS/cm about 21.0 mS/cm; and d) stopping the eluate collection when the outlet conductivity value measured for the mobile phase exiting the cation exchange chromatography column is from about 34.5 mS/cm to about 36.5 mS/cm; wherein the eluate collection comprises at least 25% of the Factor VIII retained by the cation exchange chromatography column in step (a).

11. A method of collecting an elution from a column, the method comprising the steps of: a) applying a sample comprising a Factor VIII to a cation exchange chromatography column, wherein the application causes the Factor VIII to be retained by the column; b) applying a mobile phase to the cation exchange chromatography column, the mobile phase comprising a buffered solution, wherein application of the mobile phase establishes a conductivity gradient of from about 8 mS/cm to about 90 mS/cm; c) starting an eluate collection when an inlet conductivity value measured for the mobile phase entering the cation exchange chromatography column is from about 25.0 mS/cm to about 27.0 mS/cm or an outlet conductivity value measured for the mobile phase exiting the cation exchange chromatography column is from about 19.0 mS/cm about 21.0 mS/cm; and d) stopping the eluate collection when the inlet conductivity value measured for the mobile phase entering the cation exchange chromatography column is from about 41.0 mS/cm to about 43.0 mS/cm or the outlet conductivity value measured for the mobile phase exiting the cation exchange chromatography column is from about 34.5 mS/cm to about 36.5 mS/cm; wherein the eluate collection comprises at least 25% of the Factor VIII retained by the cation exchange chromatography column in step (a).

12. A method of collecting an elution from a column, the method comprising the steps of: a) applying a sample comprising a Factor VIII to a cation exchange chromatography column, wherein the application causes the Factor VIII to be retained by the column; b) applying a mobile phase to the cation exchange chromatography column, the mobile phase comprising a buffered solution, wherein application of the mobile phase establishes a conductivity gradient of from about 8 mS/cm to about 90 mS/cm; c) starting an eluate collection when an inlet conductivity value measured for the mobile phase entering the cation exchange chromatography column is at least 21 mS/cm; and d) stopping the eluate collection when the inlet conductivity value measured for the mobile phase entering the cation exchange chromatography column is at most 47 mS/cm; wherein the eluate collection comprises at least 25% of the Factor VIII retained by the cation exchange chromatography column in step (a).

13. A method of collecting an elution from a column, the method comprising the steps of: a) applying a sample comprising a Factor VIII to a cation exchange chromatography column, wherein the application causes the Factor VIII to be retained by the column; b) applying a mobile phase to the cation exchange chromatography column, the mobile phase comprising a buffered solution, wherein application of the mobile phase establishes a conductivity gradient of from about 8 mS/cm to about 90 mS/cm; c) starting an eluate collection when an outlet conductivity value measured for the mobile phase exiting the cation exchange chromatography column is at least 15 mS/cm; and d) stopping the eluate collection when the outlet conductivity value measured for the mobile phase exiting the cation exchange chromatography column is at most 41 mS/cm; wherein the eluate collection comprises at least 25% of the Factor VIII retained by the cation exchange chromatography column in step (a).

14. A method of collecting an elution from a column, the method comprising the steps of: a) applying a sample comprising a Factor VIII to a cation exchange chromatography column, wherein the application causes the Factor VIII to be retained by the column; b) applying a mobile phase to the cation exchange chromatography column, the mobile phase comprising a buffered solution, wherein application of the mobile phase establishes a conductivity gradient of from about 8 mS/cm to about 90 mS/cm; c) starting an eluate collection when an inlet conductivity value measured for the mobile phase entering the cation exchange chromatography column is at least 21 mS/cm or an outlet conductivity value measured for the mobile phase exiting the cation exchange chromatography column is at least 15 mS/cm; and d) stopping the eluate collection when the inlet conductivity value measured for the mobile phase entering the cation exchange chromatography column is at most 47 mS/cm or the outlet conductivity value measured for the mobile phase exiting the cation exchange chromatography column is at most 41 mS/cm; wherein the eluate collection comprises at least 25% of the Factor VIII retained by the cation exchange chromatography column in step (a).

15. The embodiments of 9-14, wherein the eluate collection comprises at least 50% of the Factor VIII retained by the cation exchange chromatography column in step (a), or at least 75% of the Factor VIII retained by the cation exchange chromatography column in step (a).

16. The embodiments of 9-14, wherein the Factor VIII retained by the cation exchange chromatography column is measured by amount or an activity.

17. A method of collecting an elution from a column, the method comprising the steps of: a) applying a sample comprising a protein to an anion exchange chromatography column, wherein the application causes the protein to be retained by the column; b) applying a mobile phase to the anion exchange chromatography column, the mobile phase comprising a buffered solution, wherein application of the mobile phase establishes a conductivity gradient of from about 4 mS/cm to about 80 mS/cm; c) starting an eluate collection when an inlet conductivity value measured for the mobile phase entering the anion exchange chromatography column is from about 27.8 mS/cm to about 29.8 mS/cm; and d) stopping the eluate collection when the inlet conductivity value measured for the mobile phase entering the anion exchange chromatography column is from about 51.0 mS/cm to about 53.0 mS/cm; wherein the eluate collection comprises at least 25% of the protein retained by the anion exchange chromatography column in step (a).

18. A method of collecting an elution from a column, the method comprising the steps of: a) applying a sample comprising a protein to an anion exchange chromatography column, wherein the application causes the protein to be retained by the column; b) applying a mobile phase to the anion exchange chromatography column, the mobile phase comprising a buffered solution, wherein application of the mobile phase establishes a conductivity gradient of from about 4 mS/cm to about 80 mS/cm; c) starting an eluate collection when an outlet conductivity value measured for the mobile phase exiting the column is from about 21.0 mS/cm to about 23.0 mS/cm; and d) stopping the eluate collection when the outlet conductivity value measured for the mobile phase exiting the column is from about 45.5 mS/cm to about 47.5 mS/cm; wherein single eluate collection comprises at least 25% of the protein retained by the anion exchange chromatography column in step (a).

19. A method of collecting an elution from a column, the method comprising the steps of: a) applying a sample comprising a protein to an anion exchange chromatography column, wherein the application causes the protein to be retained by the column; b) applying a mobile phase to the anion exchange chromatography column, the mobile phase comprising a buffered solution, wherein application of the mobile phase establishes a conductivity gradient of from about 4 mS/cm to about 80 mS/cm; c) starting an eluate collection when an inlet conductivity value measured for the mobile phase entering the anion exchange chromatography column is from about 27.8 mS/cm to about 29.8 mS/cm or an outlet conductivity value measured for the mobile phase exiting the anion exchange chromatography column is from about 21.0 mS/cm to about 23.0 mS/cm; and d) stopping the eluate collection when the inlet conductivity value measured for the mobile phase entering the anion exchange chromatography column is from about 51.0 mS/cm to about 53.0 mS/cm or the outlet conductivity value measured for the mobile phase exiting the anion exchange chromatography column is from about 45.5 mS/cm to about 47.5 mS/cm; wherein single eluate collection comprises at least 25% of the protein retained by the column in step (a).

20. A method of collecting an elution from a column, the method comprising the steps of: a) applying a sample comprising a protein to an anion exchange chromatography column, wherein the application causes the protein to be retained by the column; b) applying a mobile phase to the anion exchange chromatography column, the mobile phase comprising a buffered solution, wherein application of the mobile phase establishes a conductivity gradient of from about 4 mS/cm to about 80 mS/cm; c) starting an eluate collection when an inlet conductivity value measured for the mobile phase entering the anion exchange chromatography column is at least 24 mS/cm; and d) stopping the eluate collection when the inlet conductivity value measured for the mobile phase entering the anion exchange chromatography column is from at most 57 mS/cm; wherein the eluate collection comprises at least 25% of the protein retained by the anion exchange chromatography column in step (a).

21. A method of collecting an elution from a column, the method comprising the steps of: a) applying a sample comprising a protein to an anion exchange chromatography column, wherein the application causes the protein to be retained by the column; b) applying a mobile phase to the anion exchange chromatography column, the mobile phase comprising a buffered solution, wherein application of the mobile phase establishes a conductivity gradient of from about 4 mS/cm to about 80 mS/cm; c) starting an eluate collection when an outlet conductivity value measured for the mobile phase exiting the column is at least 17 mS/cm; and d) stopping the eluate collection when the outlet conductivity value measured for the mobile phase exiting the column is at most 52 mS/cm; wherein single eluate collection comprises at least 25% of the protein retained by the anion exchange chromatography column in step (a).

22. A method of collecting an elution from a column, the method comprising the steps of: a) applying a sample comprising a protein to an anion exchange chromatography column, wherein the application causes the protein to be retained by the column; b) applying a mobile phase to the anion exchange chromatography column, the mobile phase comprising a buffered solution, wherein application of the mobile phase establishes a conductivity gradient of from about 4 mS/cm to about 80 mS/cm; c) starting an eluate collection when an inlet conductivity value measured for the mobile phase entering the anion exchange chromatography column is at least 24 mS/cm or an outlet conductivity value measured for the mobile phase exiting the anion exchange chromatography column is at least 17 mS/cm; and d) stopping the eluate collection when the inlet conductivity value measured for the mobile phase entering the anion exchange chromatography column is at most 57 mS/cm or the outlet conductivity value measured for the mobile phase exiting the anion exchange chromatography column is at most 52 mS/cm; wherein single eluate collection comprises at least 25% of the protein retained by the column in step (a).

23. The embodiments of 17-22, wherein the eluate collection comprises at least 50% of the protein retained by the anion exchange chromatography column in step (a), or at least 75% of the protein retained by the anion exchange chromatography column in step (a).

24. The embodiments of 17-22, wherein the protein retained by the anion exchange chromatography column is measured by amount or an activity.

25. A method of collecting an elution from a column, the method comprising the steps of: a) applying a sample comprising a Factor VIII to an anion exchange chromatography column, wherein the application causes the Factor VIII to be retained by the column; b) applying a mobile phase to the anion exchange chromatography column, the mobile phase comprising a buffered solution, wherein application of the mobile phase establishes a conductivity gradient of from about 4 mS/cm to about 80 mS/cm; c) starting an eluate collection when an inlet conductivity value measured for the mobile phase entering the anion exchange chromatography column is from about 27.8 mS/cm to about 29.8 mS/cm; and d) stopping the eluate collection when the inlet conductivity value measured for the mobile phase entering the anion exchange chromatography column is from about 51.0 mS/cm to about 53.0 mS/cm; wherein the eluate collection comprises at least 25% of the Factor VIII retained by the anion exchange chromatography column in step (a).

26. A method of collecting an elution from a column, the method comprising the steps of: a) applying a sample comprising a Factor VIII to an anion exchange chromatography column, wherein the application causes the Factor VIII to be retained by the column; b) applying a mobile phase to the anion exchange chromatography column, the mobile phase comprising a buffered solution, wherein application of the mobile phase establishes a conductivity gradient of from about 4 mS/cm to about 80 mS/cm; c) starting an eluate collection when an outlet conductivity value measured for the mobile phase exiting the column is from about 21.0 mS/cm to about 23.0 mS/cm; and d) stopping the eluate collection when the outlet conductivity value measured for the mobile phase exiting the column is from about 45.5 mS/cm to about 47.5 mS/cm; wherein single eluate collection comprises at least 25% of the Factor VIII retained by the anion exchange chromatography column in step (a).

27. A method of collecting an elution from a column, the method comprising the steps of: a) applying a sample comprising a Factor VIII to an anion exchange chromatography column, wherein the application causes the Factor VIII to be retained by the column; b) applying a mobile phase to the anion exchange chromatography column, the mobile phase comprising a buffered solution, wherein application of the mobile phase establishes a conductivity gradient of from about 4 mS/cm to about 80 mS/cm; c) starting an eluate collection when an inlet conductivity value measured for the mobile phase entering the anion exchange chromatography column is from about 27.8 mS/cm to about 29.8 mS/cm or an outlet conductivity value measured for the mobile phase exiting the anion exchange chromatography column is from about 21.0 mS/cm to about 23.0 mS/cm; and d) stopping the eluate collection when the inlet conductivity value measured for the mobile phase entering the anion exchange chromatography column is from about 51.0 mS/cm to about 53.0 mS/cm or the outlet conductivity value measured for the mobile phase exiting the anion exchange chromatography column is from about 45.5 mS/cm to about 47.5 mS/cm; wherein single eluate collection comprises at least 25% of the Factor VIII retained by the column in step (a).

28. A method of collecting an elution from a column, the method comprising the steps of: a) applying a sample comprising a Factor VIII to an anion exchange chromatography column, wherein the application causes the Factor VIII to be retained by the column; b) applying a mobile phase to the anion exchange chromatography column, the mobile phase comprising a buffered solution, wherein application of the mobile phase establishes a conductivity gradient of from about 4 mS/cm to about 80 mS/cm; c) starting an eluate collection when an inlet conductivity value measured for the mobile phase entering the anion exchange chromatography column is at least 24 mS/cm; and d) stopping the eluate collection when the inlet conductivity value measured for the mobile phase entering the anion exchange chromatography column is at most 57 mS/cm; wherein the eluate collection comprises at least 25% of the Factor VIII retained by the anion exchange chromatography column in step (a).

29. A method of collecting an elution from a column, the method comprising the steps of: a) applying a sample comprising a Factor VIII to an anion exchange chromatography column, wherein the application causes the Factor VIII to be retained by the column; b) applying a mobile phase to the anion exchange chromatography column, the mobile phase comprising a buffered solution, wherein application of the mobile phase establishes a conductivity gradient of from about 4 mS/cm to about 80 mS/cm; c) starting an eluate collection when an outlet conductivity value measured for the mobile phase exiting the column is at least 17 mS/cm; and d) stopping the eluate collection when the outlet conductivity value measured for the mobile phase exiting the column is at most 52 mS/cm; wherein single eluate collection comprises at least 25% of the Factor VIII retained by the anion exchange chromatography column in step (a).

30. A method of collecting an elution from a column, the method comprising the steps of: a) applying a sample comprising a Factor VIII to an anion exchange chromatography column, wherein the application causes the Factor VIII to be retained by the column; b) applying a mobile phase to the anion exchange chromatography column, the mobile phase comprising a buffered solution, wherein application of the mobile phase establishes a conductivity gradient of from about 4 mS/cm to about 80 mS/cm; c) starting an eluate collection when an inlet conductivity value measured for the mobile phase entering the anion exchange chromatography column is at least 24 mS/cm or an outlet conductivity value measured for the mobile phase exiting the anion exchange chromatography column is at least 17 mS/cm; and d) stopping the eluate collection when the inlet conductivity value measured for the mobile phase entering the anion exchange chromatography column is at most 57 mS/cm or the outlet conductivity value measured for the mobile phase exiting the anion exchange chromatography column is at most 52 mS/cm; wherein single eluate collection comprises at least 25% of the Factor VIII retained by the column in step (a).

31. The embodiments of 25-30, wherein the eluate collection comprises at least 50% of the Factor VIII retained by the anion exchange chromatography column in step (a), or at least 75% of the Factor VIII retained by the anion exchange chromatography column in step (a).

32. The embodiments of 25-30, wherein the Factor VIII retained by the anion exchange chromatography column is measured by amount or an activity.

33. The embodiments of 1-8 and 17-24, wherein the protein is a recombinant protein.

34. The embodiments of 1-8 and 17-24, wherein the protein from an organism or transgenic organism.

35. The embodiment of 33 or 34, wherein the protein is a blood protein.

36. The embodiment of 35, wherein the blood protein is a blood coagulation protein.

37. The embodiments of 33-36, wherein the blood protein is ADAMTS-13, α1-antiplasmin, α2-antiplasmin, antithrombin, antithrombin III, cancer procoagulant, erythropoietin, Factor II, Factor V, Factor VI, Factor VII, Factor VIII, Factor IX, Factor X, Factor XI, Factor XII, Factor XIII, fibronectin, fibrinogen, heparin cofactor II, highmolecular-weight kininogen, intramuscular immunoglobulin, intravenous immunoglobulin, plasminogen, plasminogen activator inhibitor-1, plasminogen activator inhibitor-2, prekallikrein, protein C, protein S, protein Z, protein Z-related protease inhibitor, tissue factor, tissue plasminogen activator, urokinase, or Von Willebrand Factor.

38. The embodiments of 1-37, wherein the buffered solution comprises 2-(N-morpholino) ethanesulfonic acid (MES), N-(2-acetamido)iminodiacetic acid (ADA), dimethylarsinic acid (Cacodylate), piperazine-N,N'-bis(2-ethanesulfonic acid) (PIPES), N-(2-Acetamido)-2-aminoethanesulfonic acid (ACES), cholamine chloride, N,N'-bis(2-hydroxyethyl)-2-aminoethanesulfonic acid (BES), 3-(N-morpholino) propanesulfonic acid (MOPS), 2-{[tris(hydroxymethyl)methyl]amino}ethanesulfonic acid (TES), N-(2-hydroxyethyl) piperazine-N'-(2-ethanesulfonic acid) (HEPES), piperazine-N,N-bis(2-hydroxypropanesulfonic acid) (POPSO), N-tris(hydroxymethyl)methylglycine (Tricine), tris(hydroxymethyl)methylamine (Tris), acetamidoglycine, N,N-bis(2-hydroxyethyl)glycine (Bicine), N-tris(hydroxymethyl)methyl-3-aminopropanesulfonic acid (TAPS), 3-[(1,1-dimethyl-2-hydroxyethyl)amino]-2-hydroxypropanesulfonic acid (AMPSO), 3-(cyclohexylamino)-2-hydroxy-1-propane-sulfonic acid (CAPSO), or 3-(cyclohexylamino)-1-propanesulfonic acid (CAPS).

39. The embodiments of 1-38, wherein the buffered solution comprises an electrolyte.

40. The embodiment of 39, wherein the electrolyte comprises sodium ions, potassium ions, calcium ions, magnesium ions, chloride ions, hydrogen phosphate ions, hydrogen carbonate ions, or any combination thereof.

41. The embodiments of 1-40, wherein the buffered solution comprises a non-ionic surfactant.

42. The embodiment of 41, wherein the non-ionic surfactant is a polyoxyethylene glycol sorbitan alkyl ester, a poloxamer, a polyoxyethylene glycol alkyl ether, a polyoxypropylene glycol alkyl ether, a glucoside alkyl ether, a dodecoxyethanol, a polyoxyethylene glycol octylphenol ether, a polyoxyethylene glycol alkylphenol ether, a glycerol alkyl ester, a sorbitan alkyl ester, a cocamide ethanolamine, sucrose monolaurate, dodecyl dimethylamine oxide, sodium cholate, or any combination thereof.

43. The embodiments of 1-42, wherein the conductivity gradient is defined by a linear function, a sigmoidal function, a logarithmic function, or an exponential function.

44. The embodiments of 1-43, wherein the method is performed as a closed system.

45. A method of collecting an elution from a column, the method comprising the steps of: a) applying a sample comprising a protein to a column, wherein the application causes the protein to be retained by the column; b) applying a mobile phase to the column, the mobile phase comprising a buffered solution, wherein application of the mobile phase establishes a conductivity gradient of from about 4 mS/cm to about 90 mS/cm; c) starting an eluate collection when an conductivity value measured for the mobile phase is from about 19.0 mS/cm to about 30.0 mS/cm; and d) stopping the eluate collection when the conductivity value measured for the mobile phase is from about 34.0 mS/cm to about 53.0 mS/cm; wherein the eluate collection comprises at least 25% of the protein retained by the column in step (a).

46. A method of collecting an elution from a column, the method comprising the steps of: a) applying a sample comprising a protein to a column, wherein the application causes the protein to be retained by the column; b) applying a mobile phase to the column, the mobile phase comprising a buffered solution, wherein application of the mobile phase establishes a conductivity gradient of from about 4 mS/cm to about 90 mS/cm; c) starting an eluate collection when an conductivity value measured for the mobile phase is at least 16 mS/cm; and d) stopping the eluate collection when the conductivity value measured for the mobile phase is at most 57 mS/cm; wherein the eluate collection comprises at least 25% of the protein retained by the column in step (a).

47. A method of collecting an elution from a column, the method comprising the steps of: a) applying a sample comprising a Factor VIII to a column, wherein the application causes the Factor VIII to be retained by the column; b) applying a mobile phase to the column, the mobile phase comprising a buffered solution, wherein application of the mobile phase establishes a conductivity gradient of from about 4 mS/cm to about 90 mS/cm; c) starting an eluate collection when an conductivity value measured for the mobile phase is from about 19.0 mS/cm to about 30.0 mS/cm; and d) stopping the eluate collection when the conductivity value measured for the mobile phase is from about 34.0 mS/cm to about 53.0 mS/cm; wherein the eluate collection comprises at least 25% of the Factor VIII retained by the column in step (a).

48. A method of collecting an elution from a column, the method comprising the steps of: a) applying a sample comprising a Factor VIII to a column, wherein the application causes the Factor VIII to be retained by the column; b) applying a mobile phase to the column, the mobile phase comprising a buffered solution, wherein application of the mobile phase establishes a conductivity gradient of from about 4 mS/cm to about 90 mS/cm; c) starting an eluate collection when an conductivity value measured for the mobile phase is at least 15 mS/cm; and d) stopping the eluate collection when the conductivity value measured for the mobile phase is at most 58 mS/cm; wherein the eluate collection comprises at least 25% of the Factor VIII retained by the column in step (a).

49. The embodiments of 45-48, wherein the column is a packed-bed chromatography column or an expanded bed adsorption chromatography column.

50. The embodiment of 49, wherein the packed-bed chromatography column is an ion exchange chromatography column, an affinity chromatography column, a hydrophobic interaction chromatography column, or a fluidized bed chromatography column.

51. The embodiment of 50, wherein the ion exchange chromatography column is a cation exchange chromatography column.

52. The embodiment of 51, wherein in step (b) the mobile phase establishes a conductivity gradient of from about 8 mS/cm to about 90 mS/cm;

53. The embodiment of 51, wherein in step (c) the conductivity value measured is an inlet conductivity value measured for the mobile phase entering the column and eluate collection starts when the inlet conductivity value is from about 25.0 mS/cm to about 27.0 mS/cm.

54. The embodiment of 51, wherein in step (d) the conductivity value measured is an inlet conductivity value measured for the mobile phase entering the column and eluate collection stops when the outlet conductivity value is from about 41.0 mS/cm to about 43.0 mS/cm.

55. The embodiment of 51, wherein in step (c) the conductivity value measured is an outlet conductivity value measured for the mobile phase exiting the column and eluate collection starts when the outlet conductivity value is from about 19.0 mS/cm about 21.0 mS/cm.
56. The embodiment of 51, wherein in step (d) the conductivity value measured is an outlet conductivity value measured for the mobile phase exiting the column and eluate collection stops when the outlet conductivity value is from about 34.5 mS/cm to about 36.5 mS/cm.
57. The embodiment of 51, wherein in step (c) the conductivity value measured is an inlet conductivity value measured for the mobile phase entering the column and eluate collection starts when the inlet conductivity value is at least 21 mS/cm.
58. The embodiment of 51, wherein in step (d) the conductivity value measured is an inlet conductivity value measured for the mobile phase entering the column and eluate collection stops when the outlet conductivity value is at most 47 mS/cm.
59. The embodiment of 51, wherein in step (c) the conductivity value measured is an outlet conductivity value measured for the mobile phase exiting the column and eluate collection starts when the outlet conductivity value is at least 15 mS/cm.
60. The embodiment of 51, wherein in step (d) the conductivity value measured is an outlet conductivity value measured for the mobile phase exiting the column and eluate collection stops when the outlet conductivity value is at most 41 mS/cm.
61. The embodiment of 50, wherein the ion exchange chromatography column is an anion exchange chromatography column.
62. The embodiment of 61, wherein in step (b) the mobile phase establishes a conductivity gradient of from about 4 mS/cm to about 80 mS/cm;
63. The embodiment of 62, wherein in step (c) the conductivity value measured is an inlet conductivity value measured for the mobile phase entering the column and eluate collection starts when the inlet conductivity value is from about 27.8 mS/cm to about 29.8 mS/cm.
64. The embodiment of 62, wherein in step (d) the conductivity value measured is an inlet conductivity value measured for the mobile phase entering the column and eluate collection stops when the outlet conductivity value is from about 51.0 mS/cm to about 53.0 mS/cm.
65. The embodiment of 62, wherein in step (c) the conductivity value measured is an outlet conductivity value measured for the mobile phase exiting the column and eluate collection starts when the outlet conductivity value is from about 21.0 mS/cm to about 23.0 mS/cm.
66. The embodiment of 62, wherein in step (d) the conductivity value measured is an outlet conductivity value measured for the mobile phase exiting the column and eluate collection stops when the outlet conductivity value is from about 45.5 mS/cm to about 47.5 mS/cm.
67. The embodiment of 62, wherein in step (c) the conductivity value measured is an inlet conductivity value measured for the mobile phase entering the column and eluate collection starts when the inlet conductivity value is at least 24 mS/cm.
68. The embodiment of 62, wherein in step (d) the conductivity value measured is an inlet conductivity value measured for the mobile phase entering the column and eluate collection stops when the outlet conductivity value is at most 57 mS/cm.
69. The embodiment of 62, wherein in step (c) the conductivity value measured is an outlet conductivity value measured for the mobile phase exiting the column and eluate collection starts when the outlet conductivity value is at least 17 mS/cm.
70. The embodiment of 62, wherein in step (d) the conductivity value measured is an outlet conductivity value measured for the mobile phase exiting the column and eluate collection stops when the outlet conductivity value is at most 52 mS/cm.
71. The embodiments of 45-70, wherein the protein is a recombinant protein.
72. The embodiments of 45-70, wherein the protein from an organism or transgenic organism.
73. The embodiment of 71 or 72, wherein the protein is a blood protein.
74. The embodiment of 73, wherein the blood protein is a blood coagulation protein.
75. The embodiment of 49-51, wherein the blood protein is ADAMTS-13, α1-antiplasmin, α2-antiplasmin, antithrombin, antithrombin III, cancer procoagulant, erythropoietin, Factor II, Factor V, Factor VI, Factor VII, Factor VIII, Factor IX, Factor X, Factor XI, Factor XII, Factor XIII, fibronectin, fibrinogen, heparin cofactor II, high-molecular-weight kininogen, intramuscular immunoglobulin, intravenous immunoglobulin, plasminogen, plasminogen activator inhibitor-1, plasminogen activator inhibitor-2, prekallikrein, protein C, protein S, protein Z, protein Z-related protease inhibitor, tissue factor, tissue plasminogen activator, urokinase, or Von Willebrand Factor.
76. The embodiments of 45-75, wherein the buffered solution comprises 2-(N-morpholino) ethanesulfonic acid (MES), N-(2-acetamido)iminodiacetic acid (ADA), dimethylarsinic acid (Cacodylate), piperazine-N,N'-bis(2-ethanesulfonic acid) (PIPES), N-(2-Acetamido)-2-aminoethanesulfonic acid (ACES), cholamine chloride, N,N'-bis (2-hydroxyethyl)-2-aminoethanesulfonic acid (BES), 3-(N-morpholino) propanesulfonic acid (MOPS), 2-{[tris (hydroxymethyl)methyl]amino}ethanesulfonic acid (TES), N-(2-hydroxyethyl) piperazine-N'-(2-ethanesulfonic acid) (HEPES), piperazine-N,N'-bis(2-hydroxypropanesulfonic acid) (POPSO), N-tris(hydroxymethyl) methylglycine (Tricine), tris(hydroxymethyl)methylamine (Tris), acetamidoglycine, N,N-bis(2-hydroxyethyl) glycine (Bicine), N-tris(hydroxymethyl)methyl-3-aminopropanesulfonic acid (TAPS), 3-[(1,1-dimethyl-2-hydroxyethyl)amino]-2-hydroxypropanesulfonic acid (AMPSO), 3-(cyclohexylamino)-2-hydroxy-1-propanesulfonic acid (CAPSO), or 3-(cyclohexylamino)-1-propanesulfonic acid (CAPS).
77. The embodiments of 45-76, wherein the buffered solution comprises an electrolyte.
78. The embodiment of 77, wherein the electrolyte comprises sodium ions, potassium ions, calcium ions, magnesium ions, chloride ions, hydrogen phosphate ions, hydrogen carbonate ions, or any combination thereof.
79. The embodiments of 45-78, wherein the buffered solution comprises a surfactant.
80. The embodiment 79, wherein the surfactant is an ionic surfactant, a zwitterionic (amphoteric) surfactant, or a non-ionic surfactant.
81. The embodiment of 80, wherein the ionic surfactant is an anion surfactant or cationic surfactant.
82. The embodiment of 81, wherein the anionic surfactant is an alkyl sulfate, an alkyl ether sulfate, a docusate, a sulfonate fluorosurfactant, an alkyl benzene sulfonate, an alkyl aryl ether phosphate, an alkyl ether phosphate, an;

alkyl carboxylate, a sodium lauroyl sarcosinate, or a carboxylate fluorosurfactant.

83. The embodiment of 82, wherein the alkyl sulfate is ammonium lauryl sulfate or sodium lauryl sulfate (SDS).

84. The embodiment of 82, wherein the alkyl ether sulfate is sodium laureth sulfate or sodium myreth sulfate.

85. The embodiment of 82, wherein the docusate is dioctyl sodium sulfosuccinate.

86. The embodiment of 82, wherein the sulfonate fluorosurfactant is perfluorooctanesulfonate (PFOS) or perfluorobutanesulfonate.

87. The embodiment of 82, wherein the alkyl carboxylate is a fatty acid salt or sodium stearate.

88. The embodiment of 82, wherein the carboxylate fluorosurfactant is perfluorononanoate and perfluorooctanoate.

89. The embodiment of 81, wherein the cationic surfactant is an alkyltrimethylammonium salt, cetylpyridinium chloride (CPC), polyethoxylated tallow amine (POEA), benzalkonium chloride (BAC), benzethonium chloride (BZT), 5-bromo-5-nitro-1,3-dioxane, dimethyldioctadecylammonium chloride, dioctadecyldimethylammonium bromide (DODAB), a pH-dependent primary amine, a pH-dependent secondary amine, or a pH-dependent tertiary amine.

90. The embodiment of 89, wherein the alkyltrimethylammonium salt is cetyl trimethylammonium bromide (CTAB) or cetyl trimethylammonium chloride (CTAC).

91. The embodiment of 89, wherein the primary amine becomes positively charged at pH<10 or the secondary amine becomes charged at pH<4.

92. The embodiment of 81, wherein the cationic surfactant is octenidine dihydrochloride.

93. The embodiment of 81, wherein the zwitterionic surfactant is 3-[(3-cholamidopropyl) dimethylammonio]-1-propanesulfonate (CHAPS), a sultaine, a, betaine, or a lecithin.

94. The embodiment of 93, wherein the sultaine is cocamidopropyl hydroxysultaine.

95. The embodiment of 93, wherein the betaine is cocamidopropyl betaine.

96. The embodiment of 81, wherein the non-ionic surfactant is a polyoxyethylene glycol sorbitan alkyl ester, a poloxamer, an alkyl phenol polyglycol ether, a polyethylene glycol alkyl aryl ether, a polyoxyethylene glycol alkyl ether, 2-dodecoxyethanol (LUBROL®-PX), a polyoxyethylene glycol octylphenol ether, a polyoxyethylene glycol alkylphenol ether, a phenoxypolyethoxylethanol, a glucoside alkyl ether, a maltoside alkyl ether, a thioglucoside alkyl ether, a digitonin, a glycerol alkyl ester, an alkyl aryl polyether sulfate, an alcohol sulfonate, a sorbitan alkyl ester, a cocamide ethanolamine, sucrose monolaurate, dodecyl dimethylamine oxide, or sodium cholate.

97. The embodiment of 96, wherein the polyoxyethylene glycol sorbitan alkyl ester is polysorbate 20 sorbitan monooleate (TWEEN® 20), polysorbate 40 sorbitan monooleate (TWEEN® 40), polysorbate 60 sorbitan monooleate (TWEEN® 60), polysorbate 61 sorbitan monooleate (TWEEN® 61), polysorbate 65 sorbitan monooleate (TWEEN® 65), polysorbate 80 sorbitan monooleate (TWEEN® 80), or polysorbate 81 sorbitan monooleate (TWEEN® 81).

98. The embodiment of 96, wherein the poloxamer is Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), or Poloxamer 407 (PLURONIC® F127).

99. The embodiment of 96, wherein the polyoxyethylene glycol alkyl ether is octaethylene glycol monododecyl ether, pentaethylene glycol monododecyl ether, BRIJ® 30, or BRIJ® 35.

100. The embodiment of 96, wherein the polyoxyethylene glycol octylphenol ether is polyoxyethylene (4-5) p-t-octyl phenol (TRITON® X-45) or polyoxyethylene octyl phenyl ether (TRITON® X-100).

101. The embodiment of 96, wherein the polyoxyethylene glycol alkylphenol ether is nonoxynol-9.

102. The embodiment of 96, wherein the phenoxypolyethoxylethanol is nonyl phenoxypolyethoxylethanol or octyl phenoxypolyethoxylethanol.

103. The embodiment of 96, wherein the glucoside alkyl ether is octyl glucopyranoside.

104. The embodiment of 96, wherein the maltoside alkyl ether is dodecyl maltopyranoside.

105. The embodiment of 96, wherein the thioglucoside alkyl ether is heptyl thioglucopyranoside.

106. The embodiment of 96, wherein the glycerol alkyl ester is glyceryl laurate.

107. The embodiment of 96, wherein the cocamide ethanolamine is cocamide monoethanolamine or cocamide diethanolamine.

108. The embodiments of 45-107, wherein the conductivity gradient is defined by a linear function, a sigmoidal function, a logarithmic function, or an exponential function.

109. The embodiments of 45-108, wherein the method is performed as a closed system.

110. The embodiments of 45, 46, or 49-109, wherein the eluate collection comprises at least 50% of the protein retained by the column in step (a), or at least 75% of the protein retained by the column in step (a).

111. The embodiment of 110, wherein the protein retained by the column is measured by amount or an activity.

112. The embodiments of 47-109, wherein the eluate collection comprises at least 50% of the Factor VIII retained by the column in step (a), or at least 75% of the Factor VIII retained by the column in step (a).

113. The embodiment of 112, wherein the Factor VIII retained by the cation exchange chromatography column is measured by amount or an activity.

114. The embodiments of 45-113, wherein the eluate collection is collected as a single elution.

115. The embodiments of 45-113, wherein the eluate collection is collected as a plurality of elutions.

116. The embodiments of 1-115 substantially as described herein.

117. A method of collecting an elution from a column substantially as described herein.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the methods of collecting an elution from a column.

Example 1

Elution from a Cation Exchange Chromatography Column

This example illustrates the methods disclosed herein for eluting a protein from a cation exchange chromatography column using a conductivity gradient disclosed herein.

Initially, a retrospective analysis of about 250 elution profiles of Factor VIII from cation exchange chromatography columns using a 24 fraction collection method was conducted. This analysis determined which fractions contained the desired threshold amount of Factor VIII. These eluate fractions were then compared to a conductivity gradient model to identify starting and stopping conductivity values.

A recombinant Factor VIII, produced by a CHO cell line that secretes the protein into the cell culture medium, was harvested by collecting the medium and centrifuging it to remove cellular debris. In a cold room kept at or below 10° C., the harvested supernatant was diluted and filtered through a 0.2 µm filter, and the Factor VIII captured by passing through an immunoaffinity chromatography column comprising immobilized α-Factor VIII mouse monoclonal antibodies and collecting the eluate. The Factor VIII was further processed by passing the immunoaffinity chromatography elution through a cation exchange chromatography column comprising 30 S cation exchange resin.

To elute the Factor VIII from the column, an elution solution comprising two buffered solutions were mixed inline and passed through the column at a constant flow rate. Buffer SA comprised 20 mM MES, 10 mM $CaCl_2 \times 2\ H_2O$, 0.1% (v/v) Polysorbate 80 and 70 mM NaCl, and has low electrical conductivity. Buffer SB comprised 20 mM MES, 10 mM $CaCl_2 \times 2\ H_2O$, 0.1% (v/v) Polysorbate 80 and 1000 mM NaCl and has high conductivity. Both buffers had a pH of about 6.35. Mixing is carried out by a mixing system comprising two valves, one connected to a vessel containing the Buffer SA and the other connected to a vessel containing the SB Buffer. A single pump is necessary to achieve the required flow rate. A linear conductivity gradient is established by progressively decreasing the proportion of Buffer SA while simultaneously increasing the proportion of Buffer SB during inline mixing. A CIT probe was positioned in front end of the cation exchange chromatography column (inlet CIT) and used for the inline measurement of conductivity. Eluate collection was started when the conductivity of the elution solution was detected by the inlet CIT probe to be about 26.0±1 mS/cm and the collection stopped when the conductivity of the elution solution was detected to be about 42.0±1 mS/cm. Alternatively, a CIT probe was positioned in back end of the cation exchange chromatography column (outlet CIT) and used for the inline measurement of conductivity. In this case, eluate collection was started when the conductivity of the elution solution was detected by the outlet CIT probe to be about 20.0±1 mS/cm and the collection stopped when the conductivity of the elution solution was detected to be about 35.5±1 mS/cm.

To assay for the amount of Factor VIII activity recovered after incubation a chromogenic assay of FVIII activity was performed. An aliquot of filtered solvent/detergent treated solution is pre-diluted in sample dilution buffer (50 mM Tris, 5 mM $CaCl_2$, 225 mM NaCl, 0.1% polysorbate 80 sorbitan monooleate (TWEEN® 80), pH 6.7±0.2) to approximately 25 IU/mL and then further diluted to 1 IU/mL in Factor VIII depleted plasma. A 100 µL prediluted sample is then mixed with 0.03 M $CaCl_2$, 0.06 mM phospholipids, 100 µL of 0.3 µM Factor IXa, 100 µL of 1 µM Factor X, and 500 µL of 3.4 µM of chromogenic substrate $CH_3OCO$-D-cyclohexylglycyl-glycyl-arginyl-p-nitroanilide to ensure that the Factor VIII is the rate limiting component of the reaction. The mixture was incubated at 37° C. for 90 seconds and then spectrophotometer readings made at 405 nm were taken to determine the rate of chromogenic substrate hydrolysis and release of p-nitro-aniline. The results obtained indicated that at least 83% of Factor VIII activity was recovered after elution using the method disclosed herein.

To assay for the amount of Factor VIII activity recovered after incubation a one-stage coagulation assay of FVIII activity was performed. An aliquot of filtered solvent/detergent treated solution is pre-diluted in sample dilution buffer (50 mM Tris, 5 mM $CaCl_2$, 225 mM NaCl, 0.1% polysorbate 80 sorbitan monooleate (TWEEN® 80), pH 6.7±0.2) to approximately 25 IU/mL and then further diluted to 1 IU/mL in Factor VIII depleted plasma. A 100 µL of prediluted sample is then mixed with 100 µL of Factor VIII deficient plasma. The mixture was incubated at 37° C. for 3 minutes and 100 µL of 25 mM $CaCl_2$ is added to start the coagulation process. The amount of Factor VIII present is determined by comparing the APTT clotting time value with a standard curve calculated by an instrument running a calculation program that makes a double logarithmic plot of the clotting time versus the factor VIII concentration. The coagulation analyzer and proper reagents for coagulation assays are designed to measure the activity of coagulation parameters in physiologic range. The results obtained indicated that at least 83% of Factor VIII activity was recovered after elution using the method disclosed herein.

To achieve reproducible and consistent elution profile of Factor VIII from repeated cation exchange chromatography column purifications, the conductivity gradient was established using a fixed volume of elution solution and time.

Example 2

Elution from an Anion Exchange Chromatography Column

This example illustrates the methods disclosed herein for eluting a protein from an anion exchange chromatography column using a conductivity gradient disclosed herein.

Initially, a retrospective analysis of about 250 elution profiles of Factor VIII from anion exchange chromatography columns using a 24 fraction collection method was conducted. This analysis determined which fractions contained the desired threshold amount of Factor VIII. These eluate fractions ere then compared to a conductivity gradient model to identify starting and stopping conductivity values.

A recombinant Factor VIII, produced by a CHO cell line that secretes the protein into the cell culture medium, was harvested by collecting the medium and centrifuging it to remove cellular debris. In a cold room kept at or below 10° C., the harvested supernatant was diluted and filtered through a 0.2 µm filter, and the Factor VIII captured by passing through an immunoaffinity chromatography column comprising immobilized α-Factor VIII mouse monoclonal antibodies and collecting the eluate. The Factor VIII was further processed by passing the immunoaffinity chromatography elution through a cation exchange chromatography column comprising negatively charged sulfonated groups. The collected eluate from this exchange column was then processed by solvent/detergent method in order to inactivate any contaminating enveloped viruses and the solvent/detergent treated eluate was then filtered through a 0.2 µm filter.

The Factor VIII was further processed by passing the filtered solution through an anion exchange chromatography column comprising Mono Q anion exchange resin.

To elute the Factor VIII from the column, an elution solution comprising two buffered solutions were mixed inline and passed through the column at a constant flow rate. Buffer QA comprised 50 mM Tris, 5 mM $CaCl_2 \times 2$ $H_2O$, 0.1% (v/v) Polysorbate 80, and has low electrical conductivity. Buffer QB comprised 50 mM Tris, 5 mM $CaCl_2 \times 2$ $H_2O$, 0.1% (v/v) Polysorbate 80 and 750 mM NaCl and has high conductivity. Both buffers had a pH of about 6.7. Mixing is carried out by a mixing system comprising two valves, one connected to a vessel containing the Buffer QA and the other connected to a vessel containing the QB Buffer. A single pump is necessary to achieve the required flow rate. A linear conductivity gradient is established by progressively decreasing the proportion of Buffer QA while simultaneously increasing the proportion of Buffer QB during inline mixing. A CIT probe was positioned in front end of the anion exchange chromatography column (inlet CIT) and used for the inline measurement of conductivity. Eluate collection was started when the conductivity of the elution solution was detected by the inlet CIT probe to be about 28.8±1 mS/cm and the collection stopped when the conductivity of the elution solution was detected to be about 52.0±1 mS/cm. Alternatively, a CIT probe was positioned in back end of the anion exchange chromatography column (outlet CIT) and used for the inline measurement of conductivity. In this case, eluate collection was started when the conductivity of the elution solution was detected by the outlet CIT probe to be about 22.0±1 mS/cm and the collection stopped when the conductivity of the elution solution was detected to be about 46.5±1 mS/cm.

To assay for the amount of Factor VIII activity recovered after elution a chromogenic assay of FVIII activity was performed essentially as described in Example 1. The results obtained indicated that at least 83% of Factor VIII activity was recovered after elution using the method disclosed herein.

To assay for the amount of Factor VIII activity recovered after elution a one-stage coagulation assay of FVIII activity was performed essentially as described in Example 1. The results obtained indicated that at least 83% of Factor VIII activity was recovered after elution using the method disclosed herein.

To achieve reproducible and consistent elution profile of Factor VIII from repeated anion exchange chromatography column purifications, the conductivity gradient was established using a fixed volume of elution solution and time.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method of collecting an elution from a column, said method comprising the steps of:
    a) applying a sample comprising a Factor VIII protein to a cation exchange chromatography column, wherein said Factor VIII protein is retained by said cation exchange chromatography column;
    b) applying a mobile phase to said cation exchange chromatography column, said mobile phase comprising a buffered solution, wherein said mobile phase establishes a conductivity gradient of from about 4 mS/cm to about 90 mS/cm in said cation exchange chromatography column;
    c) starting a single fraction eluate collection, wherein said single fraction eluate collection includes a single start conductivity value and a single stop conductivity value, wherein said single start conductivity value starts when an inlet conductivity value measured for said mobile phase of step b) enters said cation exchange chromatography column at about 25.0 mS/cm to about 27.0 mS/cm and when an outlet conductivity value measured for said mobile phase of step b) enters said cation exchange chromatography column at about 19.0 mS/cm to about 21.0 mS/cm; and
    d) stopping said single faction eluate collection when said single stop conductivity value measured for said mobile phase of step b) at the inlet is from about 41.0 mS/cm to about 43.0 mS/cm and said single stop conductivity value measured for said mobile phase of step b) at the outlet is from about 34.5 mS/cm to about 36.5 mS/cm; and wherein said single fraction eluate collection comprises 83% Factor VIII protein activity retained by said cation exchange chromatography column in step a).

2. The method of claim 1, wherein in step (b) said mobile phase establishes a conductivity gradient of from about 8 mS/cm to about 90 mS/cm.

3. The method of claim 1, wherein said Factor VIII protein is a recombinant protein or a protein from an organism or a transgenic organism.

4. A method of collecting an elution from a column, the method comprising the steps of:
    a) applying a sample comprising a Factor VIII protein to an anion exchange chromatography column, wherein said Factor VIII protein is retained by said anion exchange chromatography column;
    b) applying a mobile phase to said anion exchange chromatography column, said mobile phase comprising a buffered solution, wherein said mobile phase establishes a conductivity gradient of from about 4 mS/cm to about 80 mS/cm in said anion exchange chromatography column;
    c) starting a single fraction eluate collection, wherein said single fraction eluate collection includes a single start conductivity value and a single stop conductivity value, wherein said single start conductivity value starts when an inlet conductivity value measured for said mobile phase of step b) enters said anion exchange chromatography column at about 27.8 mS/cm to about 29.8 mS/cm and when an outlet conductivity value measured for said mobile phase of step b) enters said anion exchange chromatography column at about 21.0 mS/cm to about 23.0 mS/cm; and
    d) stopping said single fraction eluate collection when said single stop conductivity value measured for said mobile phase of step b) at the inlet is from about 51.0 mS/cm to about 53.0 mS/cm and said single stop conductivity value measured for mobile phase of step b) at the outlet is from about 45.5 mS/cm to about 47.5 mS/cm; and wherein said single fraction eluate collection comprises 83% Factor VIII protein activity retained by said anion exchange chromatography column in step (a).

5. The method of claim 4, wherein said Factor VIII protein is a recombinant protein or a protein from an organism or a transgenic organism.

* * * * *